(12) United States Patent
Cheng et al.

(10) Patent No.: US 12,397,024 B2
(45) Date of Patent: Aug. 26, 2025

(54) **MULTI-*LACTOBACILLUS* COMPOSITION AND APPLICATION THEREOF TO VAGINAL HEALTH OF FEMALES**

(71) Applicant: SICHUAN ANAEROBIC BIOTECHNOLOGY CO., LTD., Sichuan (CN)

(72) Inventors: Lei Cheng, Sichuan (CN); Yao Liu, Sichuan (CN); Qiong Wang, Sichuan (CN); Wanqiu Zeng, Sichuan (CN)

(73) Assignee: SICHUAN ANAEROBIC BIOTECHNOLOGY CO., LTD., Sichuan (CN)

( * ) Notice: Subject to any disclaimer, the term of this patent is extended or adjusted under 35 U.S.C. 154(b) by 677 days.

(21) Appl. No.: 17/435,670

(22) PCT Filed: Aug. 7, 2020

(86) PCT No.: PCT/CN2020/107915
§ 371 (c)(1),
(2) Date: Sep. 1, 2021

(87) PCT Pub. No.: WO2021/027740
PCT Pub. Date: Feb. 18, 2021

(65) Prior Publication Data
US 2022/0133819 A1    May 5, 2022

(30) Foreign Application Priority Data
Aug. 9, 2019    (CN) .......................... 201910732792.4

(51) Int. Cl.
*A61K 35/747*    (2015.01)
*A61P 15/02*    (2006.01)

(52) U.S. Cl.
CPC ............ *A61K 35/747* (2013.01); *A61P 15/02* (2018.01)

(58) Field of Classification Search
CPC ......... A61K 35/747; A61K 8/99; A61P 15/02; A61P 31/04; C12R 2001/225; A61L 15/36; A61L 15/44; A61L 15/46; C12N 1/20; C12N 1/205; Y02A 50/30; A23L 33/135; A61Q 19/00; A23V 2002/00; A23V 2200/30
See application file for complete search history.

(56) References Cited

U.S. PATENT DOCUMENTS

| | | | |
|---|---|---|---|
| 2006/0194226 A1 | 8/2006 | Liu et al. | |
| 2013/0171253 A1 | 7/2013 | Kiss et al. | |
| 2017/0071990 A1* | 3/2017 | De Seta | A61K 9/4858 |
| 2018/0117100 A1 | 5/2018 | Ko et al. | |

FOREIGN PATENT DOCUMENTS

| | | |
|---|---|---|
| CN | 102851248 A | 1/2013 |
| CN | 107794236 A | 3/2018 |
| CN | 107815432 A | 3/2018 |
| CN | 108004187 A | 5/2018 |
| CN | 108354952 A | 8/2018 |
| CN | 110656060 A | 1/2020 |
| KR | 20170109446 A | 9/2017 |
| WO | 2006083516 A2 | 8/2006 |
| WO | 2018013583 A2 | 1/2018 |
| WO | 2018064978 A1 | 4/2018 |

OTHER PUBLICATIONS

Ventura et al. (Appl Environ Microbiol, 2002, 68:6172) (Year: 2002).*
Wu, Zhongmei et al. "Research progress on Lactobacillus and its application in the treatment of vaginitis", Journal of Modern Medicine and Health, Jun. 30, 2018, vol. 34, No. 12, pp. 1851-1854.

* cited by examiner

*Primary Examiner* — David Steadman
*Assistant Examiner* — Joseph R Spangler
(74) *Attorney, Agent, or Firm* — NKL Law; Allen Xue

(57) ABSTRACT

A multi-lactobacillus composition is a dominant strain separated and selected from the vagina of a healthy woman in China. The multi-lactobacillus composition comprises at least three of the following active components: *Lactobacillus johnsonii, Lactobacillus gasseri, Lactobacillus rhamnosus, Lactobacillus crispatus*, and *Lactobacillus jensenii*.

17 Claims, 6 Drawing Sheets
Specification includes a Sequence Listing.

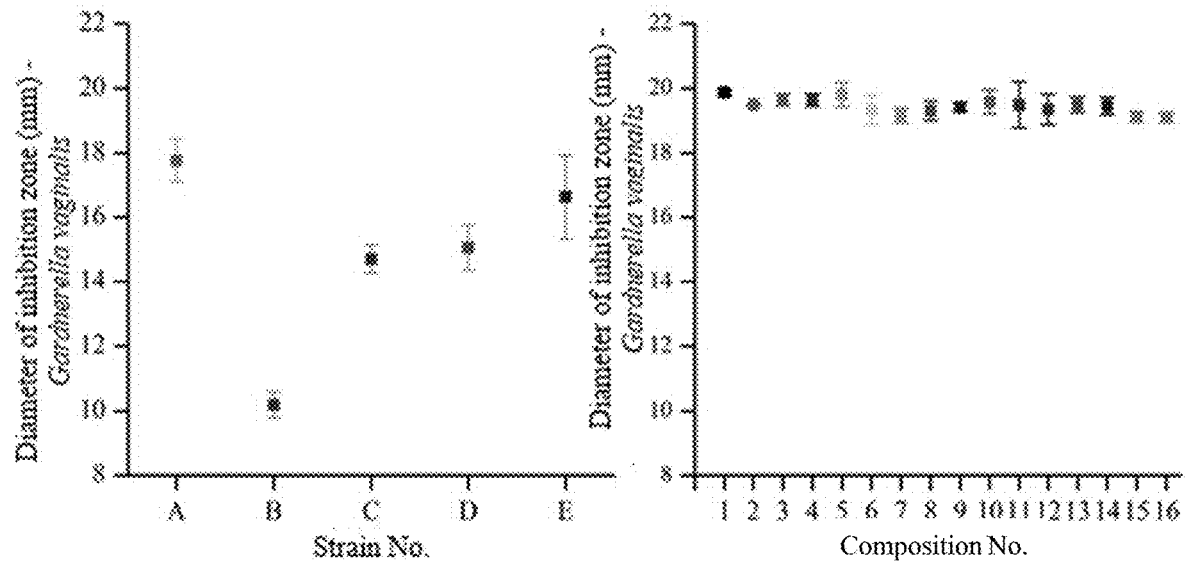
FIG. 3A  FIG. 3B
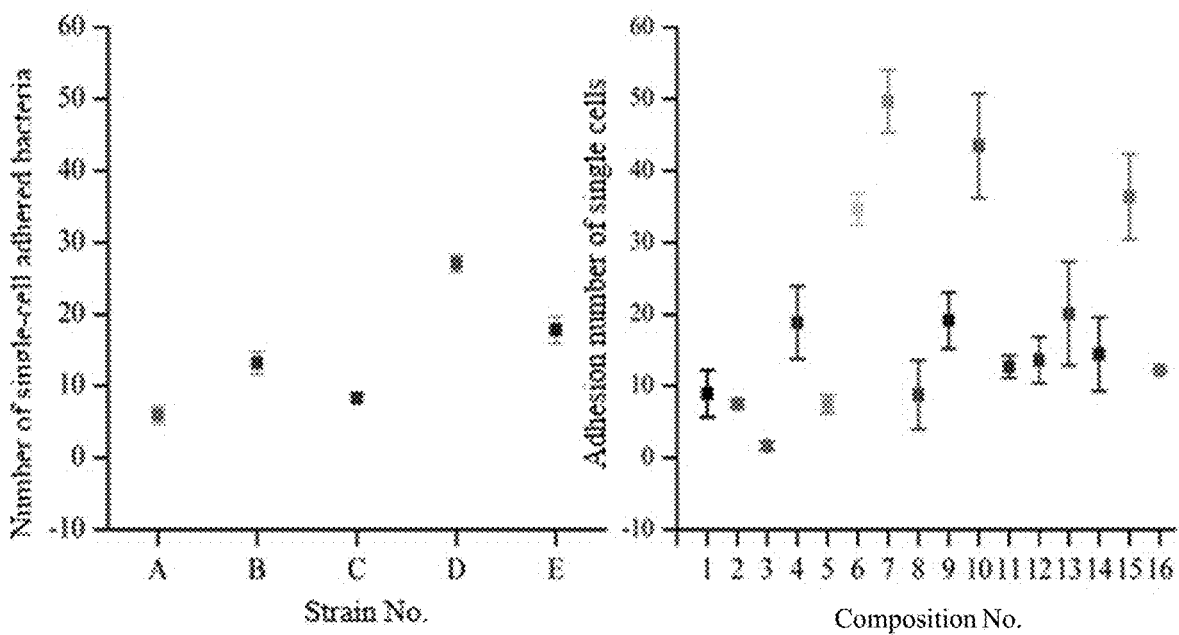
FIG. 4A  FIG. 4B

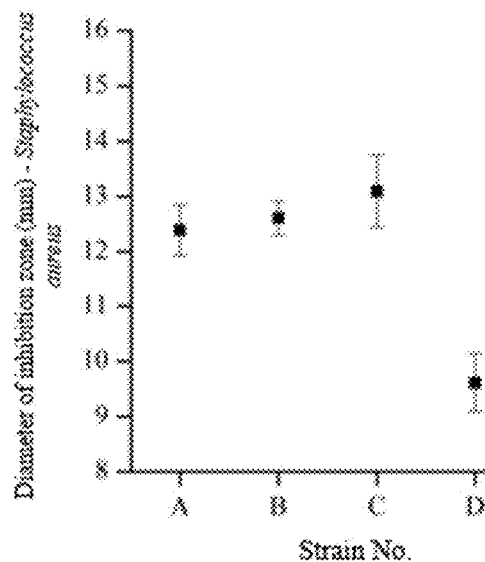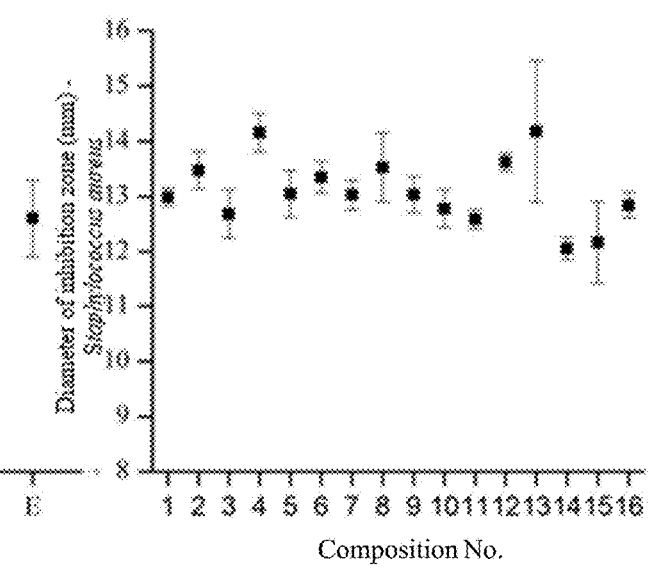
FIG. 5A    FIG. 5B
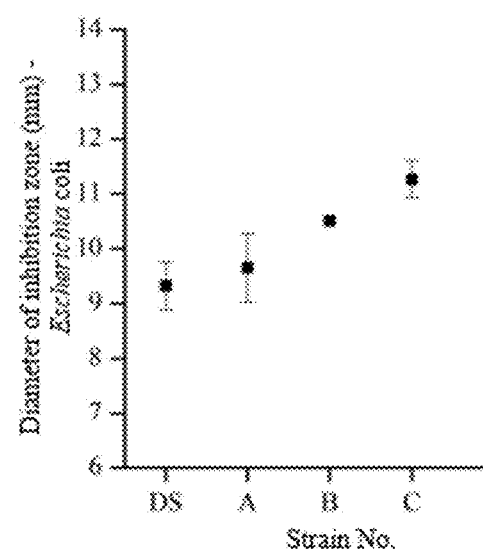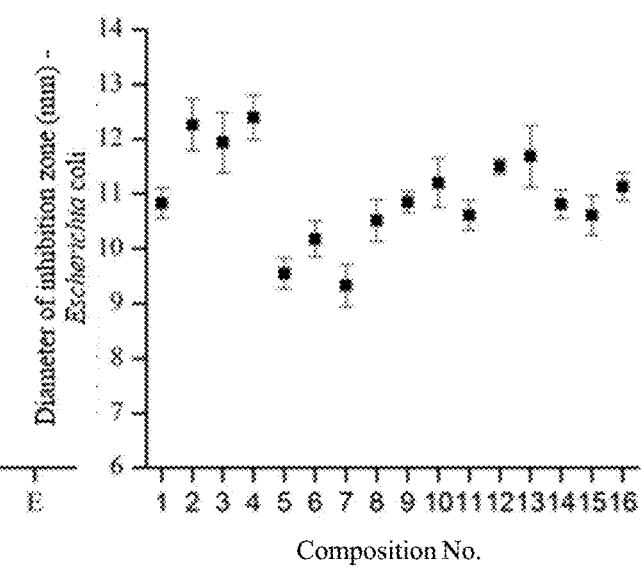
FIG. 6A    FIG. 6B

```
                              SEQUENCE LISTING

<160> NUMBER OF SEQ ID NOS: 5

<210> SEQ ID NO 1
<211> LENGTH: 1461
<212> TYPE: DNA
<213> ORGANISM: Lactobacillus sp.

<400> SEQUENCE: 1
gctcgctccc taaagggtta cgccaccggc ttcgggtgtt acaaactctc atggtgtgac      60
gggcggtgtg tacaaggccc gggaacgtat tcaccgcggc gtgctgatcc gcgattacta     120
gcgattccga cttcgtgtag gcgagttgca gcctacagtc cgaactgaga atggctttaa     180
gagattagct tgacctcgcg gtctcgcaac tcgttgtacc atccattgta gcacgtgtgt     240
agcccaggtc ataaggggca tgatgatttg acgtcatccc caccttcctc cggtttgtca     300
ccggcagtct tactagagtg cccaactaaa tgctggcaac tagtcataag ggttgcgctc     360
gttgcgggac ttaacccaac atctcacgac acgagctgac gacaaccatg caccacctgt     420
cattttgccc ccgaagggga aacctgatct ctcaggtgat caaaagatgt caagacctgg     480
taaggttctt cgcgttgctt cgaattaaac cacatgctcc accgcttgtg cgggcccccg     540
tcaattcctt tgagtttcaa ccttgcggtc gtactcccca ggcggaatgc ttaatgcgtt     600
agctgcggca ctgaagggcg gaaaccctcc aacacctagc attcatcgtt tacggcatgg     660
actaccaggg tatctaatcc tgttcgctac ccatgctttc gagcctcagc gtcagttaca     720
gaccagacag ccgccttcgc cactggtgtt cttccatata tctacgcatt tcaccgctac     780
acatggagtt ccactgtcct cttctgcact caagtttccc agtttccgat gcacttcctc     840
ggttaagccg agggctttca catcagactt aaaaaaccgc ctgcgctcgc tttacgccca     900
ataaatccgg ataacgcttg ccacctacgt attaccgcgg ctgctggcac gtagttagcc     960
gtggctttct ggttggatac cgtcacgccg acaacagtta tctgccgac cattcttctc    1020 caacaacaga gttttacgac ccgaaagcct tcttcactca cgcggcgttg ctccatcaga    1080
cttgcgtcca ttgtggaaga ttccctactg ctgcctcccg taggagtttg ggccgtgtct    1140
cagtcccaat gtggccgatc aacctctcag ttcggctacg tatcattgcc ttggtgagcc    1200
gttacctcac caactagcta atacgccgcg ggtccatcca aaagcgatag cttacgccat    1260
ctttcagcca agaaccatgc ggttcttgga tttatgcggt attagcatct gtttccaaat    1320
gttatccccc acttaagggc aggttaccca cgtgttactc acccgtccgc cactcgttca    1380
aaattaaatc aagatgcaag cacctttcaa taatcagaac tcgttcgact tgcatgtatt    1440
aggcacgccg ccagcggtca t                                              1461

<210> SEQ ID NO 2
<211> LENGTH: 1437
<212> TYPE: DNA
<213> ORGANISM: Lactobacillus johnsonii

<400> SEQUENCE: 2
gctgatccta taaggttat cccaccggct ttgggtgtta cagactctca tggtgtgacg      60
ggcggtgtgt acaaggcccg ggaacgtatt caccgcggcg tgctgatccg cgattactag    120
```

```
cgattccagc ttcgtgtagg cgagttgcag cctacagtcc gaactgagaa cggctttaag    180
agatccgctt gccttcgcag gttcgcttct cgttgtaccg tccattgtag cacgtgtgta    240
gcccaggtca taaggggcat gatgacttga cgtcatcccc accttcctcc ggtttgtcac    300
cggcagtctc attagagtgc ccaacttaat gatggcaact aatgacaagg gttgcgctcg    360
ttgcgggact taacccaaca tctcacgaca cgagctgacg acagccatgc accacctgtc    420
tcagcgtccc cgaagggaac acctaatctc ttaggtttgc actggatgtc aagacctggt    480
aaggttcttc gcgttgcttc gaattaaacc acatgctcca ccgcttgtgc gggccccgt     540
caattccttt gagtttcaac cttgcggtcg tactccccag gcggagtgct taatgcgtta    600
gctgcagcac tgagaggcgg aaacctccca acacttagca ctcatcgttt acggcatgga    660
ctaccagggt atctaatcct gttcgctacc catgctttcg agcctcagcg tcagttgcag    720
accagagagc cgccttcgcc actggtgttc ttccatatat ctacgcattc caccgctaca    780
catggagttc cactctcctc ttctgcactc aagttcaaca gtttctgatg caattctccg    840
gttgagccga aggctttcac atcagactta ttgaaccgcc tgcactcgct ttacgcccaa    900
taaatccgga caacgcttgc cacctacgta ttaccgcggc tgctggcacg tagttagccg    960
tgactttcta agtaattacc gtcaaataaa ggccagttac tacctctatc tttcttcact   1020
accaacagag ctttacgagc cgaaaccctt cttcactcac gcggcgttgc tccatcagac   1080
tttcgtccat tgtggaagat tccctactgc tgcctcccgt aggagtttgg gccgtgtctc   1140
agtcccaatg tggccgatca gtctctcaac tcggctatgc atcattgcct tggtaagccg   1200
ttaccttacc aactagctaa tgcaccgcag gtccatccaa gagtgatagc agaaccatct   1260
ttcaaactct agacatgcgt ctagtgttgt tatccggtat tagcatctgt ttccaggtgt   1320
tatcccagtc tcttgggcag gttacccacg tgttactcac ccgtccgccg ctcgcttgta   1380
tctagtttca tttagtgcaa gcactaaaat catctaggca agctcgctcg actgcag      1437
```

<210> SEQ ID NO 3
<211> LENGTH: 1437
<212> TYPE: DNA
<213> ORGANISM: Lactobacillus gasseri

<400> SEQUENCE: 3

```
gctgatccta taaaggttat cccaccggct ttgggtgtta cagactctca tggtgtgacg     60
ggcggtgtgt acaaggcccg ggaacgtatt caccgcggcg tgctgatccg cgattactag    120
cgattccagc ttcgtgtagg cgagttgcag cctacagtcc gaactgagaa cggctttcag    180
agatccgctt gccttcgcag gttcgcttct cgttgtaccg tccattgtag cacgtgtgta    240
gcccaggtca taaggggcat gatgacttga cgtcatcccc accttcctcc ggtttgtcac    300
cggcagtctc attagagtgc ccaacttaat gatggcaact aatgacaagg gttgcgctcg    360
ttgcgggact taacccaaca tctcacgaca cgagctgacg acagccatgc accacctgtc    420
tcagcgtccc cgaagggaac acctaatctc ttaggtttgc actggatgtc aagacctggt    480
aaggttcttc gcgttgcttc gaattaaacc acatgctcca ccgcttgtgc gggccccgt     540
caattccttt gagtttcaac cttgcggtcg tactccccag gcggagtgct taatgcgtta    600
gctgcagcac tgagaggcgg aaacctccca acacttagca ctcatcgttt acggcatgga    660
ctaccagggt atctaatcct gttcgctacc catgctttcg agcctcagcg tcagttgcag    720
accagagagc cgccttcgcc actggtgttc ttccatatat ctacgcattc caccgctaca    780
catggagttc cactctcctc ttctgcactc aagttcaaca gtttctgatg caattctccg    840
```

```
gttgagccga aggctttcac atcagactta ttgaaccgcc tgcactcgct ttacgcccaa      900
taaatccgga caacgcttgc cacctacgta ttaccgcggc tgctggcacg tagttagccg      960
tgactttcta agtaattacc gtcaaataaa ggccagttac tacctctatc tttcttcact     1020
accaacagag ctttacgagc cgaaacccct tcttcactcac gcggcgttgc tccatcagac    1080
ttgcgtccat tgtggaagat tccctactgc tgcctcccgt aggagtttgg gccgtgtctc     1140
agtcccaatg tggccgatca gtctctcaac tcggctatgc atcattgcct tggtaagccg     1200
ttaccttacc aactagctaa tgcaccgcag gtccatccaa gagtgatagc agaaccatct     1260
tttaaactct agacatgcgt ctagtgttgt tatccggtat tagcatctgt ttccaggtgt     1320
tatcccagtc tcttgggcag gttacccacg tgttactcac ccgtccgccg ctcgcttgta     1380
tctagtttca tttggtgcaa gcaccaaatt catctaggca agctcgctcg actgcag       1437
```

<210> SEQ ID NO 4
<211> LENGTH: 1461
<212> TYPE: DNA
<213> ORGANISM: Lactobacillus rhamnosus
<400> SEQUENCE: 4

```
gctcgctccc taagggggtta cgccaccggc ttcgggtgtt acaaactctc atggtgtgac     60
gggcggtgtg tacaaggccc gggaacgtat tcaccgcggc gtgctgatcc gcgattacta    120
gcgattccga cttcgtgtag gcgagttgca gcctacagtc gaactgaga atggctttaa     180 gagattagct tgacctcgcg gtctcgcaac tcgttgtacc atccattgta gcacgtgtgt     240
agcccaggtc ataaggggca tgatgatttg acgtcatccc caccttcctc cggtttgtca     300
ccggcagtct tactagagtg cccaactaaa tgctggcaac tagtcataag ggttgcgctc     360
gttgcgggac ttaacccaac atctcacgac acgagctgac gacaaccatg caccacctgt     420
cattttgccc ccgaagggga aacctgatct ctcaggtgat caaaagatgt caagacctgg    480
taaggttctt cgcgttgctt cgaattaaac cacatgctcc accgcttgtg cgggccccg     540 tcaattcctt tgagtttcaa ccttgcggtc gtactcccca ggcggaatgc ttaatgcgtt    600
agctgcggca ctgaagggcg gaaaccctcc aacacctagc attcatcgtt tacggcatgg    660
actaccaggg tatctaatcc tgttcgctac ccatgctttc gagcctcagc gtcagttaca    720
gaccagacag ccgccttcgc cactggtgtt cttccatata tctacgcatt tcaccgctac    780
acatggagtt ccactgtcct cttctgcact caagtttccc agtttccgat gcacttcctc    840
ggttaagccg agggctttca catcagactt aaaaaaccgc ctgcgctcgc tttacgccca    900
ataaatccgg ataacgcttg ccacctacgt attaccgcgg ctgctggcac gtagttagcc    960
gtggctttct ggttggatac cgtcacgccg acaacagtta tctgccgac cattcttctc    1020 caacaacaga gttttacgac ccgaaagcct tcttcactca cgcggcgttg ctccatcaga    1080
cttgcgtcca ttgtggaaga ttccctactg ctgcctcccg taggagtttg ggccgtgtct    1140
cagtcccaat gtggccgatc aacctctcag ttcggctacg tatcattgcc ttggtgagcc    1200
gttacctcac caactagcta atacgccgcg gtccatcca aaagcgatag cttacgccat     1260 cttttcagcca agaaccatgc ggttcttgga tttatgcggt attagcatct gtttccaaat    1320
gttatccccc acttaagggc aggttaccca cgtgttactc accgtccgc cactcgttca    1380 aaattaaatc aagatgcaag caccctttcaa taatcagaac tcgttcgact tgcatgtatt   1440
aggcacgccg ccagcggtca t                                               1461
```

<210> SEQ ID NO 5
<211> LENGTH: 1425
<212> TYPE: DNA
<213> ORGANISM: Lactobacillus crispatus

<400> SEQUENCE: 5

| | | | | | |
|---|---|---|---|---|---|
| cttccgaagg | ttaggccacc | ggctttgggc | attgcagact | cccatggtgt | gacgggcggt | 60 |
| gtgtacaagg | cccgggaacg | tattcaccgc | ggcgtgctga | tccgcgatta | ctagcgattc | 120 |
| cagcttcgtg | cagtcgagtt | gcagactgca | gtccgaactg | agaacagctt | tcagagattc | 180 |
| gcttgccttc | gcaggctcgc | ttctcgttgt | actgcccatt | gtagcacgtg | tgtagcccag | 240 |
| gtcataaggg | gcatgatgac | ttgacgtcat | ccccaccttc | ctccggtttg | tcaccggcag | 300 |
| tctcattaga | gtgcccaact | taatgctggc | aactaataac | aagggttgcg | ctcgttgcgg | 360 |
| gacttaaccc | aacatctcac | gacacgagct | gacgacagcc | atgcaccacc | tgtcttagcg | 420 |
| tccccgaagg | gaactttgta | tctctacaaa | tggcactaga | tgtcaagacc | tggtaaggtt | 480 |
| cttcgcgttg | cttcgaatta | aaccacatgc | tccaccgctt | gtgcgggccc | ccgtcaattc | 540 |
| ctttgagttt | caaccttgcg | gtcgtactcc | ccaggcggag | tgcttaatgc | gttagctgca | 600 |
| gcactgagag | gcggaaacct | cccaacactt | agcactcatc | gtttacggca | tggactacca | 660 |
| gggtatctaa | tcctgttcgc | tacccatgct | ttcgagcctc | agcgtcagtt | gcagaccaga | 720 |
| gagccgcctt | cgccactggt | gttcttccat | atatctacgc | attccaccgc | tacacatgga | 780 |
| gttccactct | cctcttctgc | actcaagaaa | aacagtttcc | gatgcagttc | ctcggttaag | 840 |
| ccgagggctt | tcacatcaga | cttattcttc | cgcctgcgct | cgctttacgc | ccaataaatc | 900 |
| cggacaacgc | ttgccaccta | cgtattaccg | cggctgctgg | cacgtagtta | gccgtgactt | 960 |
| tctggttgat | taccgtcaaa | taaggccag | ttactacctc | tatccttctt | caccaacaac | 1020 |
| agagctttac | gatccgaaaa | ccttcttcac | tcacgcggcg | ttgctccatc | agacttgcgt | 1080 |
| ccattgtgga | agattcccta | ctgctgcctc | ccgtaggagt | ttgggccgtg | tctcagtccc | 1140 |
| aatgtggccg | atcagtctct | caactcggct | atgcatcatc | gccttggtaa | gcctttacct | 1200 |
| taccaactag | ctaatgcacc | gcggggccat | cccatagcga | cagcttacgc | cgccttttaa | 1260 |
| aagctgatca | tgcgatctgc | tttcttatcc | ggtattagca | cctgtttcca | agtggtatcc | 1320 |
| cagactatgg | ggcaggttcc | ccacgtgtta | ctcacccatc | cgccgctcgc | tttcctaacg | 1380 |
| tcattaccga | agtaaatctg | ttattccgct | cgctcgactg | cagtt | | 1425 |

MULTI-*LACTOBACILLUS* COMPOSITION AND APPLICATION THEREOF TO VAGINAL HEALTH OF FEMALES

INCORPORATION OF SEQUENCE LISTING

This application contains a sequence listing submitted in Computer Readable Form (CRF). The CFR file containing the sequence listing entitled "PA119-0062_ST25.txt", which was created on Aug. 20, 2021, and is 10,278 bytes in size. The information in the sequence listing is incorporated herein by reference in its entirety.

TECHNICAL FIELD

The present disclosure relates to the field of microorganisms, and in particular to a multi-lactobacillus composition and an application thereof to vaginal health of females.

BACKGROUND

According to the *Research Progress and Clinical Significance of Vaginal Microecology* published by the Journal of Practical Obstetrics and Gynecology, the *Advances in Research on Survival State of Lactobacillus in Vaginal Microecology* published by the Chinese Journal of Microecology and other research reports, there are over 300 symbiotic microorganisms in human vagina. They inter-restrict and inter-convert with each other to form a dynamic balance. Hence, various kinds of vaginitis are caused by an unbalance in a vaginal microecological environment.

The vagina of a health female of child-bearing age is a micro-environment with the lactobacilli as a dominant flora. They may not only grow by virtue of glycogen inside the vaginal epithelial cells and produce $H_2O_2$, lactic acid and bacteriocin, but also may be competitively adhered to the vaginal epithelium to occupy a binding site and digest endovaginal nutrients, thereby dominating in the vagina and inhibiting the excessive proliferation of other pathogenic bacteria and anaerobes. Researches over the last decade have found that lactobacilli are very diverse in human vagina, different lactobacilli play a synergistic role in the vaginal microenvironment, and the lactobacilli are different in different domains and populations. In macroscopic view, the dominant bacteria in the vaginas of the healthy females from different races are significantly different (according to research, 80%-90% of Asians and the white race have lactobacilli as the dominant bacteria, but less than 60% of black women and Spanish have lactobacilli as the dominant bacteria). In microscopic view, there are individual differences in the dominant lactobacilli between different individuals. At present, over 20 lactobacilli have been separated from the vaginal microenvironment. The vaginal ecological flora of the females in North American may be divided into five types. There are four dominant bacteria, including *Lactobacillus crispatus, Lactobacillaus iners, Lactobacillus jensenii* and *Lactobacillus gasseri*. The fifth is other lactobacilli and anaerobes. The most common dominant lactobacilli in the vaginas of the health females in China includes *Lactobacillus crispatus, Lactobacillus gasseri, Lactobacillus jensenii, Lactobacillus rhamnosus, Lactobacillus reuteri, Lactobacillus johnsonii, Lactobacillus acidophilus* and *Lactobacillus iners*.

When any environment factor or external intervention breaks through the vaginal microecological balance, the vaginal microecological environment will enter a fragile state, thus uneasily resisting against reproduction or invasion of the pathogenic bacteria to cause various kinds of vaginitis. Bacterial vaginosis (hereinafter referred to as the "BV") is a common gynecological disease, with an infection rate of 15%-52%. It is a vaginal infectious disease which is a clinical syndrome for vaginal dysbacteriosis caused by excessive reproduction of *Gardnerella vaginalis* and other anaerobes to substitute the lactobacilli. It is reported that the BV is a hazard factor to cause histologic chorioamnionitis, amniotic fluid infection, postcesarean endometritis and other poor pregnancy symptoms and pregnancy complications.

For the clinical treatment method, the BV is treated with metronidazole or clindamycin. The metronidazole is a prod-rug, namely, in an anaerobic environment, a nitryl of the metronidazole is reduced to an amino through bacterial intracellular enzymatic reduction, so as to convert antibiotics into active forms, and then covalently bonds to a DNA to damage a helical structure thereof and break single and double strands, thereby realizing DNA degradation and pathogen death; and the clindamycin may bind to a 50S ribosomal subunit on a bacterial ribosome to prevent prolongation of a peptide chain, thus restraining protein synthesis of bacterial cells and causing bacterial death. Antibiotic therapy is quick in effect, but has two considerable defects, including: (1) With an inhibiting effect on all antibiotic sensitive microorganisms in the vaginal microenvironment, the restrained or killed pathogenic microorganisms and alien pathogenic microorganisms will reproduce again to cause vaginitis recurrence or new vaginitis if a vaginal microecosystem does not restore to a healthy balance state against the invasion of pathogenic bacteria upon treatment. (2) The refractory BV will be caused by a drug resistance of the microorganisms and failure of the antibiotics to balance the vaginal microecological environment. Hence, the antibiotic therapy is quick in effect, but the recurrence rate is high, up to 30% in three months.

Treatment for vaginal microecological imbalance includes sterilization, mucous membrane and restoration of vaginal microecological balance. Sterilization is the first step to treat the vaginitis namely restraining or killing the pathogenic microorganisms including excessively proliferated aerobes and anaerobes, blastospores or hyphae, and trichomonads. After the pathogenic microorganisms are restrained or killed, the ultimate goal to treat the vaginitis is the immune repair of the vaginal mucosa and the restoration of the dominant lactobacilli. In this time, if the recovery of the vaginal mucosa or the restoration of the dominant lactobacilli is affected and an endovaginal physicochemical environment is not restored to normal, the restrained or alien pathogenic microorganisms will reproduce again, even cause vaginitis reoccurrence or new vaginitis. Probiotics may quickly occupy vaginal epithelial receptors in the vagina to protect the vagina, thereby promoting the vagina to restore to a normal microenvironment and reduce the recurrence of the vaginitis. Therefore, a probiotic microecologics is an optimal method to treat the BV from the perspective of the current technical means.

Only two kinds of vaginal microecologics have been sold in China. The first one is a commercially available drug (trade name: "Danhua") produced by Xi'an Zhenghao Biology Pharmacy Limited Company, including *Streptococcus faecalis*, which is not a vaginal dominant species, and moreover, the bacteria of the species are conditionally pathogenic; and the other one is a commercially available drug (trade name: "Wanze Shuangqi") produced by Inner Mongolia Shuangqi Pharmaceutical Co., Ltd., including one lactobacillus—*Lactobacillus delbrueckii*, which does not belong to the dominant species in the vaginas of the females in China. Therefore, it is more advantageous to treat the BV with the vaginal microecologics prepared by the dominant lactobacilli strain.

Chinese patent document CN102851248 A discloses *Lactobacillus jensenii* for preventing and curing bacterial vaginosis, wherein the *Lactobacillus jensenii* is a dominant *Lactobacillus* separated from the vagina of a health female bodies in China. Chinese patent document CN 107794236 A discloses *Lactobacillus crispatus* and an application thereof, wherein the *Lactobacillus crispatus* is a dominant *Lactobacillus* separated from the vagina of a health female in China for treating the B V. Chinese patent document CN 108004187 A discloses *Lactobacillus gasseri* and an application thereof for preparing vaginal bacteriostatic drugs, wherein the *Lactobacillus gasseri* is a dominant *Lactobacillus* separated from the vagina of a health female in China. In addition to the foregoing listed three Chinese patent documents, there are many similar related patent documents about dominant lactobacilli separated from the vaginas of the health females in China and applications for treating the BV thereof. All of them are to treat the BV with the single *Lactobacillus* screened from the vaginas of the health females in China.

With various and abundant lactobacilli in the human vagina, different lactobacilli show different probiotic abilities, and play a synergistic role in the vaginal microenvironment. Moreover, for the individual differences, the dominant strains in the vaginas of different females are slightly different. Hence, it is necessary to take into comprehensive consideration the varieties of the lactobacilli and the probiotic abilities of different species while considering the vaginal lactobacillus probiotics. This shows that the BV must be treated with the vaginal microecologics prepared by mixing the dominant lactobacilli due to not wide treatment range of the BV with the single strain.

SUMMARY

The present disclosure aims to, with respect to the problems in the prior art, provide a multi-lactobacillus composition belonging to a dominant strain in the vaginas of females in China. The strains are mutualistic without antagonism, and has a synergistic effect to produce a stronger probiotic ability than a single dominant strain. Moreover, a multi-lactobacillus is more widely used in the treatment of bacterial vaginosis (BV).

The multi-lactobacillus composition provided by the present disclosure is the dominant strain separated and screened from the vaginas of the healthy females in China. To be specific, the multi-lactobacillus composition at least comprises three of the following active ingredients:

*Lactobacillus johnsonii, Lactobacillus gasseri, Lactobacillus rhamnosus, Lactobacillus crispatus* and *Lactobacillus jensenii*.

It is especially worth highlighting that the *Lactobacillus johnsonii* is *Lactobacillus johnsonii* Ljohn-1; the *Lactobacillus gasseri* is *Lactobacillus gasseri* Lgass-17; the *Lactobacillus rhamnosus* is *Lactobacillus rhamnosus* Lrham-6; the *Lactobacillus* crispatus is *Lactobacillus* crispatus Lcris-2; and the *Lactobacillus jensenii* is *Lactobacillus jensenii* Ljen-10. The foregoing various lactobacilli are screened and separated from the vaginas of the health females in China. Under the provisions of the Budapest Treaty on the International Recognition of the Deposit of Microorganisms for the Purposes of Patent Procedure, the foregoing various lactobacilli were deposited with the international depositary authority: China Center for Type Culture Collection (CCTCC), Wuhan University, Wuhan 430072 P.R. China, on Jun. 4, 2019. Specifically, *Lactobacillus johnsonii* Ljohn-1 was deposited under the Accession Number: 2019426, *Lactobacillus gasseri* Lgass-17 was deposited under the Accession Number: 2019430, *Lactobacillus rhamnosus* Lrham-6 was deposited under the Accession Number: 2019428; *Lactobacillus* crispatus Lcris-2 was deposited under the Accession Number: 2019427; and *Lactobacillus jensenii* Ljen-10 was deposited under the Accession Number: 2019429. All restrictions imposed by the depositor on the availability to the public of the deposited material will be irrevocably removed upon the granting of a patent.

After being uploaded to EzBiocloud, a complete genome sequence of the *Lactobacillus rhamnosus* Lrham-6 is compared with all complete genome sequences of conspecies that it can link to obtain an average nucleotide identity (ANI) ratio as shown in Table 1, proving that it is a new *Lactobacillus* strain.

TABLE 1

ANI Comparison of Complete Genomes of Lrham-6 and Different *Lactobacillus Rhamnosus*

| Name of sequential document | Species of reference document | Name of reference document | ANI (%) |
| --- | --- | --- | --- |
| Lrham-6.genomic.fasta | *Lactobacillus rhamnosus* | GCA_002406795.1_ASM240679v1_genomic.fna.gz | 99.9524 |
| Lrham-6.genomic.fasta | *Lactobacillus rhamnosus* | GCA_002406745.1_ASM240674v1_genomic.fna.gz | 99.9515 |
| Lrham-6.genomic.fasta | *Lactobacillus rhamnosus* | GCA_002406715.1_ASM240671v1_genomic.fna.gz | 99.9506 |
| Lrham-6.genomic.fasta | *Lactobacillus rhamnosus* | GCA_000173255.2_ASM17325v2_genomic.fna.gz | 99.9388 |
| Lrham-6.genomic.fasta | *Lactobacillus rhamnosus* | GCA_002406785.1_ASM240678v1_genomic.fna.gz | 99.9366 |
| Lrham-6.genomic.fasta | *Lactobacillus rhamnosus* | GCA_001812155.1_ASM181215v1_genomic.fna.gz | 99.8953 |
| Lrham-6.genomic.fasta | *Lactobacillus rhamnosus* | GCA_001062955.1_ASM106295v1_genomic.fna.gz | 99.7943 |
| Lrham-6.genomic.fasta | *Lactobacillus rhamnosus* | GCA_001064785.1_ASM106478v1_genomic.fna.gz | 99.7669 |
| Lrham-6.genomic.fasta | *Lactobacillus rhamnosus* | GCA_001657135.1_ASM165713v1_genomic.fna.gz | 99.6405 |
| Lrham-6.genomic.fasta | *Lactobacillus rhamnosus* | GCA_001062885.1_ASM106288v1_genomic.fna.gz | 99.6173 |

After being uploaded to EzBiocloud, a complete genome sequence of the *Lactobacillus gasseri* Lgass-17 is compared with all complete genome sequences of conspecies that it can link to obtain an average nucleotide identity (ANI) ratio as shown in Table 2, proving that it is a new *Lactobacillus* strain.

TABLE 2

ANI Comparison of Complete Genomes of Lgass-17 and Different *Lactobacillus Gasseri*

| Name of sequential document | Species of reference document | Name of reference document | ANI (%) |
| --- | --- | --- | --- |
| Lgass-17.genomic.fasta | *Lactobacillus gasseri* | GCA_000177035.2_ASM17703v2_genomic.fna.gz | 99.9256 |
| Lgass-17.genomic.fasta | *Lactobacillus gasseri* | GCA_000177415.1_ASM17741v1_genomic.fna.gz | 99.8912 |
| Lgass-17.genomic.fasta | *Lactobacillus gasseri* | GCA_000176995.2_ASM17699v2_genomic.fna.gz | 99.7935 |
| Lgass-17.genomic.fasta | *Lactobacillus gasseri* | GCA_001063045.1_ASM106304v1_genomic.fna.gz | 99.776 |
| Lgass-17.genomic.fasta | *Lactobacillus gasseri* | GCA_001066235.1_ASM106623v1_genomic.fna.gz | 99.7531 |
| Lgass-17.genomic.fasta | *Lactobacillus gasseri* | GCA_000439915.1_*L.gasseri*_2016_V1_genomic.fna.gz | 99.7284 |
| Lgass-17.genomic.fasta | *Lactobacillus gasseri* | GCA_001063065.1_ASM106306v1_genomic.fna.gz | 99.7232 |
| Lgass-17.genomic.fasta | *Lactobacillus gasseri* | GCA 000014425.1_ASM1442v1_genomic.fna.gz | 99.6302 |
| Lgass-17.genomic.fasta | *Lactobacillus gasseri* | GCA_000155935.2_Lacto_*gasseri*_MV-22_V2_genomic.fna.gz | 99.5271 |
| Lgass-17.genomic.fasta | *Lactobacillus gasseri* | GCA_000283135.1_ASM28313v1_genomicfna.gz | 99.2187 |

After being uploaded to EzBiocloud, a complete genome sequence of the *Lactobacillus johnsonii* Ljohn-1 is compared with all complete genome sequences of conspecies that it can link to obtain an average nucleotide identity (ANI) ratio as shown in Table 3, proving that it is a new *Lactobacillus* strain.

TABLE 3

ANI Comparison of Complete Genomes of Ljohn-1 and Different *Lactobacillus Johnsonii*

| Name of sequential document | Species of reference document | Name of reference document | ANI (%) |
| --- | --- | --- | --- |
| Ljohn-1.genomic.fasta | *Lactobacillus johnsonii* | GCA_000498675.1_ASM49867v1_enomic.fna.gz | 95.5668 |
| Ljohn-1.genomic.fasta | *Lactobacillus johnsonii* | GCA_002253275.1_ASM225327v1_genomic.fna.gz | 95.4233 |
| Ljohn-1.genomic.fasta | *Lactobacillus johnsonii* | GCA_002253205.1_ASM225320v1_genomic.fna.gz | 95.3823 |
| Ljohn-1.genomic.fasta | *Lactobacillus johnsonii* | GCA_002253165.1_ASM225316v1_genomic.fna.gz | 95.3732 |
| Ljohn-1.genomic.fasta | *Lactobacillus johnsonii* | GCA_002253185.1_ASM225318v1_genomic.fna.gz | 95.3683 |
| Ljohn-1.genomic.fasta | *Lactobacillus johnsonii* | GCA_002253245.1_ASM225324v1_genomic.fna.gz | 95.3515 |
| Ljohn-1.genomic.fasta | *Lactobacillus johnsonii* | GCA_002253285.1_ASM225328v1_genomic.fna.gz | 95.3379 |
| Ljohn-1.genomic.fasta | *Lactobacillus johnsonii* | GCA_001270785.1_ASM127078v1_genomic.fna.gz | 95.3079 |
| Ljohn-1.genomic.fasta | *Lactobacillus johnsonii* | GCA_001572665.1_ASM157266v1_genomic.fna.gz | 95.1633 |
| Ljohn-1.genomic.fasta | *Lactobacillus johnsonii* | GCA_002803395.1_ASM280339v1_genomic.fna.gz | 95.0963 |

After being uploaded to EzBiocloud, a complete genome sequence of the *Lactobacillus jensenii* Ljen-10 is compared with all complete genome sequences of conspecies that it can link to obtain an average nucleotide identity (ANI) ratio as shown in Table 4, proving that it is a new *Lactobacillus* strain.

TABLE 4

ANI Comparison of Complete Genomes of Ljen-10 and Different *Lactobacillus Jensenii*

| Name of sequential document | Species of reference document | Name of reference document | ANI (%) |
|---|---|---|---|
| Ljen-10.genomic.fasta | *Lactobacillus jensenii* | GCA_002848045.1_ASM284804v1_genomic.fna.gz | 88.9784 |
| Ljen-10.genomic.fasta | *Lactobacillus jensenii* | GCA_000155915.2_Lacto_*jensenii*_1153_v2_genomic.fna.gz | 88.7036 |
| Ljen-10.genomic.fasta | *Lactobacillus jensenii* | GCA_001936235.1_ASM193623v1_genomic.fna.gz | 88.6759 |
| Ljen-10.genomic.fasta | *Lactobacillus jensenii* | GCA_002863405.1_ASM286340v1_genomic.fna.gz | 88.6432 |
| Ljen-10.genomic.fasta | *Lactobacillus jensenii* | GCA_000466805.1_ASM46680v1_genomic.fna.gz | 88.5848 |
| Ljen-10.genomic.fasta | *Lactobacillus jensenii* | GCA_000162335.1_ASM16233v1_genomic.fna.gz | 88.5791 |
| Ljen-10.genomic.fasta | *Lactobacillus jensenii* | GCA_000175035.1_ASM17503v1_genomic.fna.gz | 88.5055 |
| Ljen-10.genomic.fasta | *Lactobacillus jensenii* | GCA_001436455.1_ASM143645v1_genomic.fna.gz | 88.4346 |
| Ljen-10.genomic.fasta | *Lactobacillus jensenii* | GCA_001012665.1_IM18-1v1_genomic.fna.gz | 88.4042 |
| Ljen-10.genomic.fasta | *Lactobacillus jensenii* | GCA_001012685.1_IM18-3v1_genomic.fna.gz | 88.3924 |

After being uploaded to EzBiocloud, a complete genome sequence of the *Lactobacillus crispatus* Lcris-2 compared with all complete genome sequences of conspecies that it can link to obtain an average nucleotide identity (ANI) ratio as shown in Table 5, proving that it is a new *Lactobacillus* strain.

TABLE 5

ANI Comparison of Complete Genomes of Lcris-2 and Different *Lactobacillus Crispatus*

| Name of sequential document | Species of reference document | Name of reference document | ANI (%) |
|---|---|---|---|
| Lcris-2.genomic.fasta | *Lactobacillus crispatus* | GCA_002861765.1_ASM286176v1_genomic.fna.gz | 99.3638 |
| Lcris-2.genomic.fasta | *Lactobacillus crispatus* | GCA_001546015.1_ASM154601v1_genomic.fna.gz | 99.2264 |
| Lcris-2.genomic.fasta | *Lactobacillus crispatus* | GCA_000176975.2_ASM17697v2_genomic.fna.gz | 99.2008 |
| Lcris-2.genomic.fasta | *Lactobacillus crispatus* | GCA_001546025.1_ASM154602v1_genomic.fna.gz | 99.1693 |
| Lcris-2.genomic.fasta | *Lactobacillus crispatus* | GCA_001541585.1_ASM154158v1_genomic.fna.gz | 99.0587 |
| Lcris-2.genomic.fasta | *Lactobacillus crispatus* | GCA_001541515.1_ASM154151v1_genomic.fna.gz | 99.0447 |
| Lcris-2.genomic.fasta | *Lactobacillus crispatus* | GCA_000301135.1_Lact_cris_FB077-07_V1_genomic.fna.gz | 99.0328 |
| Lcris-2.genomic.fasta | *Lactobacillus crispatus* | GCA_002861775.1_ASM286177v1_genomic.fna.gz | 99.0016 |
| Lcris-2.genomic.fasta | *Lactobacillus crispatus* | GCA_000466885.2_ASM46688v2_genomic.fna.gz | 98.9705 |
| Lcris-2.genomic.fasta | *Lactobacillus crispatus* | GCA_000301115.1_Lact_cris_FB049-03_V1_genomic.fna.gz | 98.9698 |

A viable count of the multi-lactobacillus composition is $10^5$-$10^{11}$ CFU/g, and a content of each single bacteria is not lower than $10^5$ CFU/g.

According to the present disclosure, a bacteriological preparation with the above multi-lactobacillus composition as an active ingredient may be a suspension or lyophilized bacteria powder.

According to the present disclosure, the multi-lactobacillus composition is applied to preparation of drugs or health care products for preventing or treating pathogenic bacteria of bacterial vaginosis (B V). According to the present disclosure, the multi-lactobacillus composition may be applied to preparation of sanitary articles for pudendum, such as sanitary napkins, tampons or health care solution for pudendum.

According to the present disclosure, the multi-lactobacillus composition may be applied to preparation of drugs or health care products for adjusting the balance of vaginal flora.

According to the present disclosure, the multi-lactobacillus composition may be applied to preparation of drugs or health care products with an adhesion function of vaginal epithelial cells.

According to the present disclosure, the multi-lactobacillus composition may be applied to preparation of drugs, health care products and food additives for preventing and treating the pathogenic bacteria, and the pathogenic bacteria include but not limited to any one or more of *Gardnerella vaginalis*, *Staphylococcus aureus*, *Pseudomonas aeruginosa*, *Escherichia coli*, *Salmonella* paratyphi B and *Shigella dysenteriae*.

The multi-lactobacillus composition may be also applied to preparation of external care products for infants delivered by caesarean section. The infants delivered by caesarean section will not get exogenous probiotics during their birth because they are not born through female vagina. For this reason, the probiotics screened from the vaginas of the females may be prepared into external care products to daub or wash the infant bodies.

Compared with the prior art, the present disclosure has the following beneficial effects:

With diverse strains of lactobacilli colonized in the vaginas of the health females, different strains of different or same species have different probiotic abilities. Hence, there is a necessity to take into comprehensive consideration the varieties of lactobacilli, lactic acid and hydrogen peroxide production capacities, inhibition of pathogenic bacteria and adhesion on vaginal cells while considering the vaginal lactobacillus probiotics. In order to cover as many females with vaginal dysbacteriosis as possible, and meanwhile, strengthen the ability to inhibit different pathogenic bacteria, the inventor will carry out reasonable compatibility for proper strains from a variety of strains separated and screened from the health females in China, and use the separated and screened lactobacilli to prevent and treat the B V by virtue of three or more *Lactobacillus* combination formulas. Through experimental verification, the multi-lactobacillus composition has the better probiotic ability, and belongs to the dominant strain in the vaginas of the females in China. Accordingly, it is expected that the multi-lactobacillus composition will have the better effect to treat and prevent vaginal diseases of Chinese females, and also has a wide cover range.

BRIEF DESCRIPTION OF DRAWINGS

FIGS. 3A and 3B are diagrams that show comparison of inhibitions on *Gardnerella vaginalis* by single bacteria and combined bacteria.

FIGS. 4A and 4B are diagrams that show comparison of adhesions on hela cells by single bacteria and combined bacteria.

FIGS. 5A and 5B are diagrams that show comparison of inhibitions on *Staphylococcus aureus* by single bacteria and combined bacteria.

FIGS. 6A and 6B are diagrams that show comparison of inhibitions on *Escherichia coli* by single bacteria and combined bacteria.

DESCRIPTION OF EMBODIMENTS

Figures 1A, 1B:
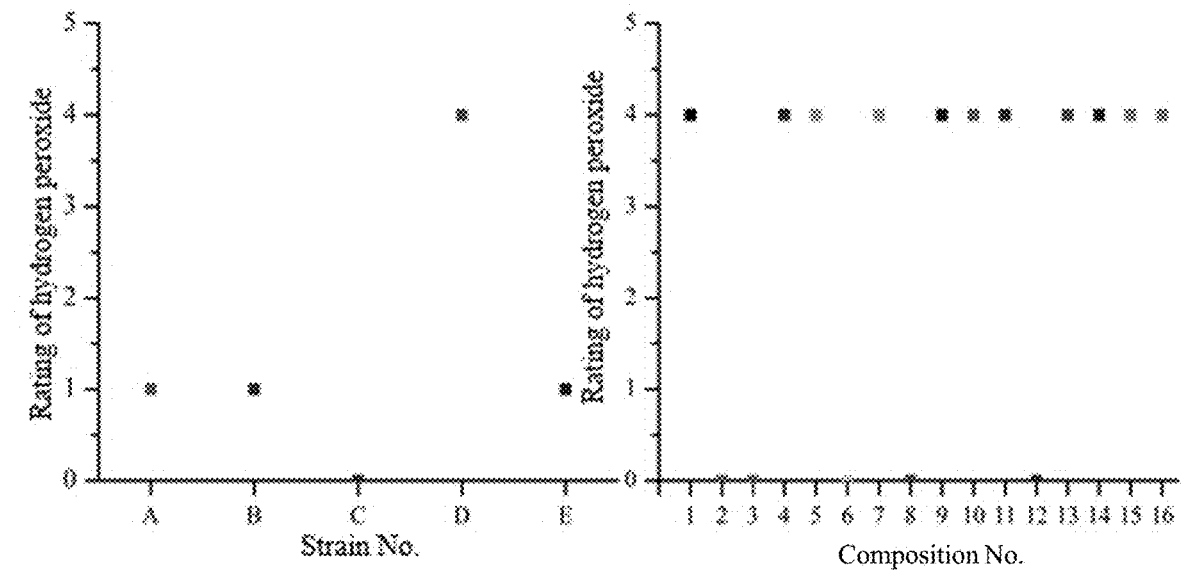
FIGS. 1A and 1B are diagrams that show comparison of rating of hydrogen peroxide production capacities of single bacteria and combined bacteria.
Figures 2A, 2B:
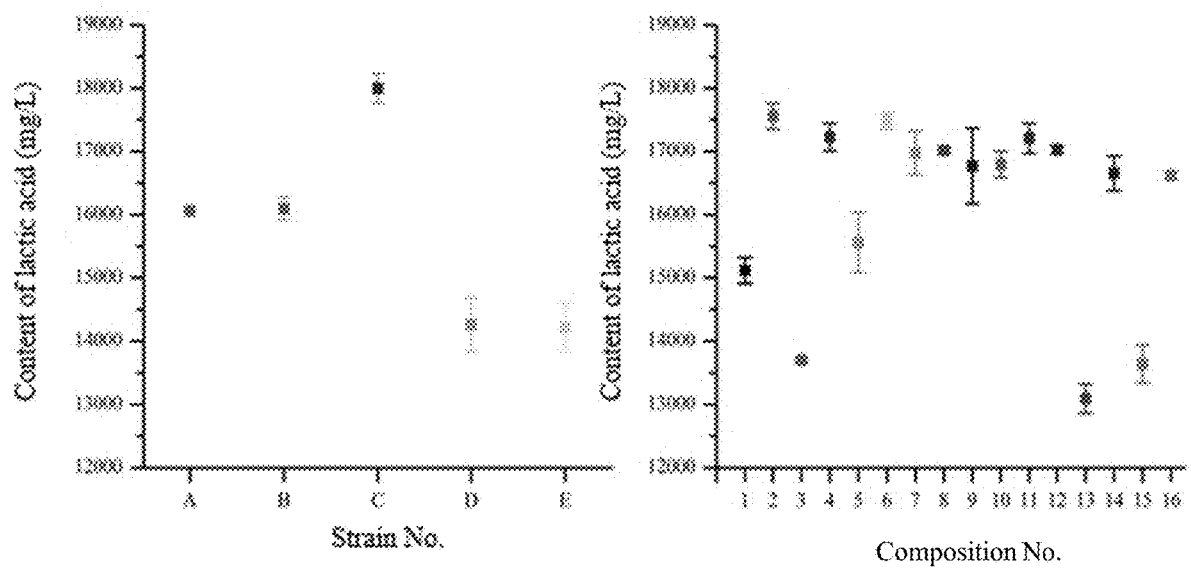
FIGS. 2A and 2B are diagrams that show comparison of lactic acid production capacities of single bacteria and combined bacteria.
Figures 7A, 7B:
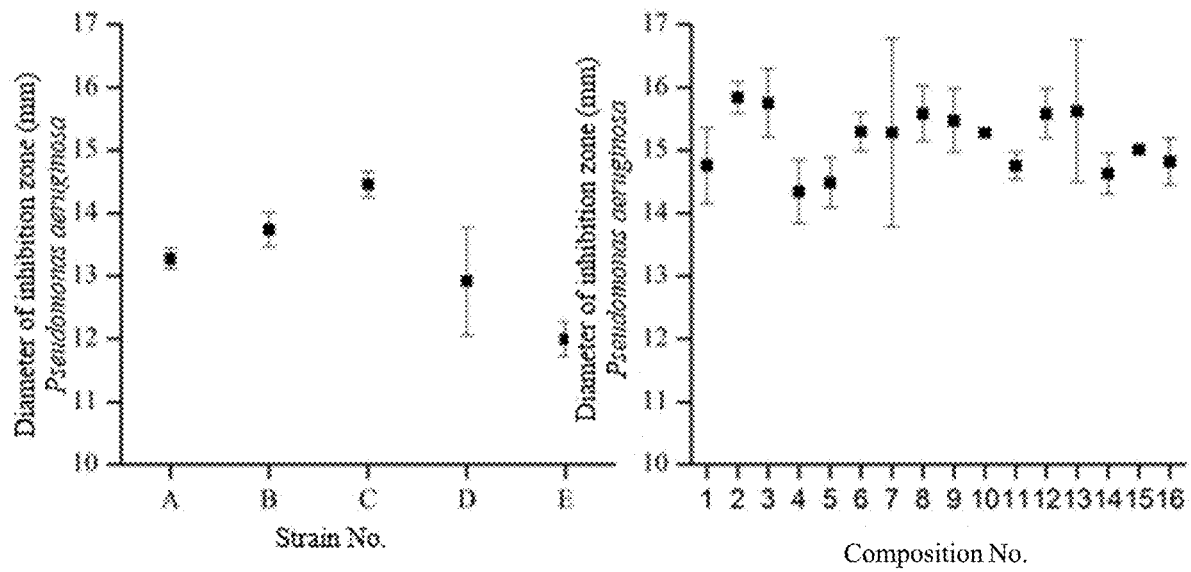
FIGS. 7A and 7B are diagrams that show comparison of inhibitions on *Pseudomonas aeruginosa* by single bacteria and combined bacteria.
Figures 8A, 8B:
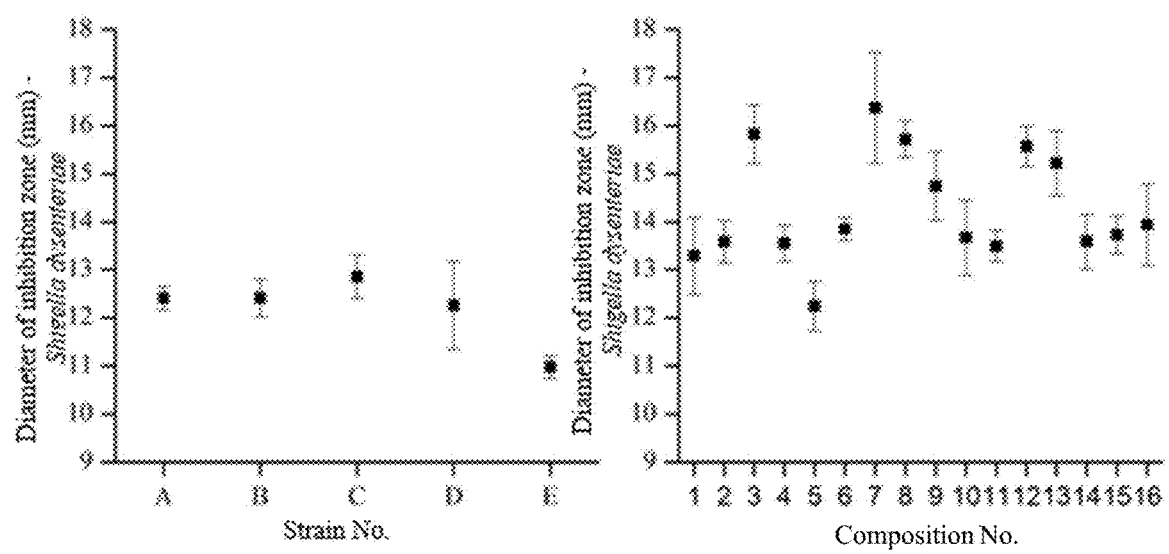
FIGS. 8A and 8B are diagrams that show comparison of inhibitions on *Shigella dysenteriae* by single bacteria and combined bacteria.
Figure 9A:
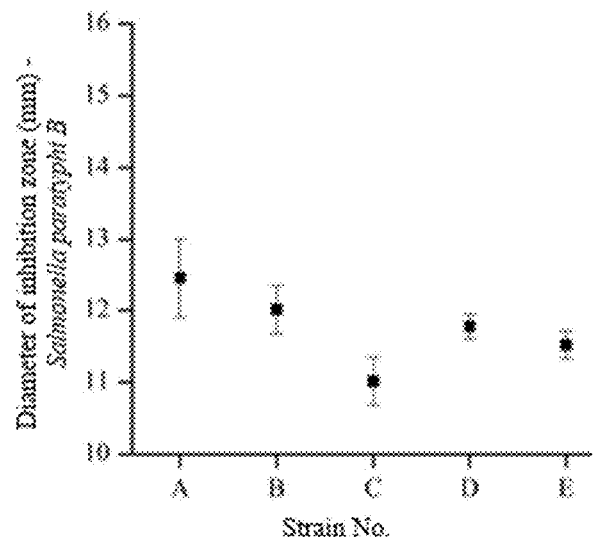
FIGS. 9A and 9B are diagrams that show comparison of inhibitions on *Salmonella* paratyphi B by single bacteria and combined bacteria.
Figure 9B:
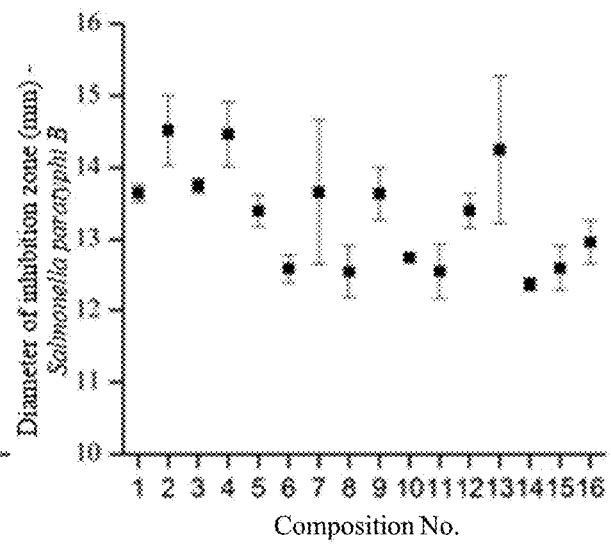
Figure 10:
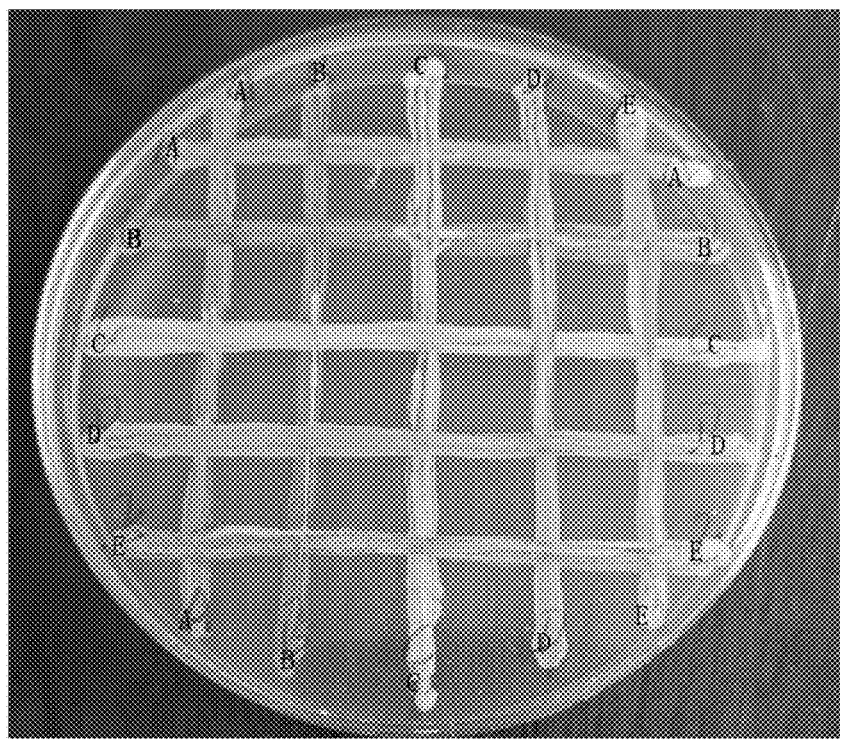
FIG. 10 is a test diagram 1 of a solid symbiotic effect between all single bacteria in multi-*lactobacillus*.
Figure 11:
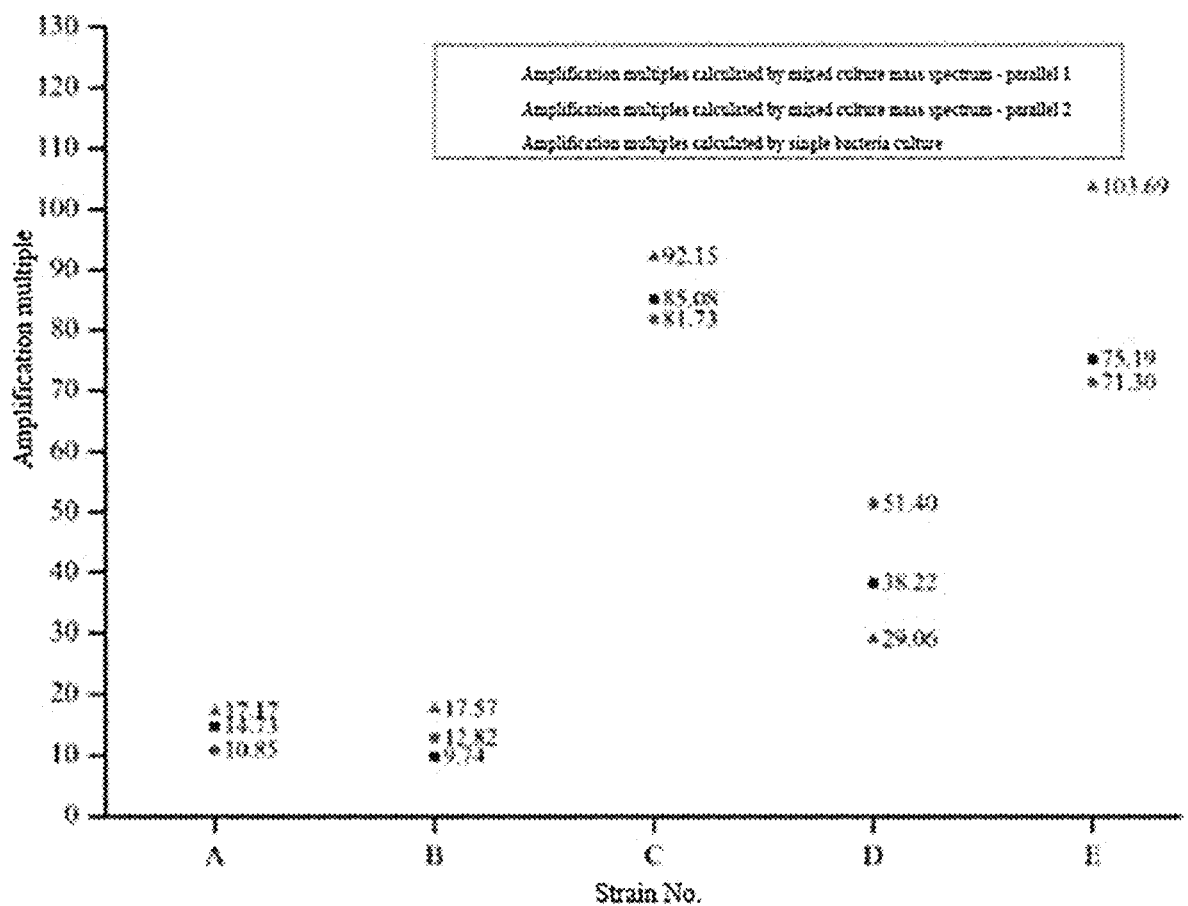
FIG. 11 is a test diagram 2 of a symbiotic effect of a broth between all single bacteria in multi-*lactobacillus*.

The following paragraphs will elaborate the specific implementations of the present disclosure, and the implementations of the present disclosure include but not limited to the following embodiments. In an attempt to prevent excessive unnecessary details, the public structures or functions will not be elaborated in the following embodiments. Unless otherwise defined, all technical and scientific terms used in the following embodiments have the same meanings as those commonly appreciated by those of ordinary skilled in the art to which this disclosure belongs. All reagent consumables used in the following embodiments are common biochemical reagents without otherwise specified.

A method for screening and separating *Lactobacillus johnsonii* Ljohn-1, *Lactobacillus gasseri* Lgass-17, *Lactobacillus crispatus* Lcris-2, *Lactobacillus jensenii* Ljen-10, and *Lactobacillus rhamnosus* Lrham-6 is as follows:

Collecting a vaginal secretion sample of a female, aged 20-40, passing physical examination in China with a vaginal cotton swab; filling 2 mL of sterile anaerobic PBS buffer solution into an anaerobic tube with the cotton swab, shaking fully for mixing uniformly, and diluting as a stock solution by ten consecutive gradients; coating 100 μL of liquid diluted to 10,000 times to a MRS solid medium, cultivating in an anaerobic incubator at 37° C., selecting a single colony of suspected lactobacillus to cultivate for 24 h in a MRS broth medium after cultivating for 48 h, continuously transferring one part of bacteria solution obtained upon cultivation for continuous cultivation, and extracting bacterial DNA from the other part of bacteria solution; and obtaining 1,336 lactobacilli in total by virtue of carrying out bacteria 16S rRNA gene amplification and sequencing, carrying out BLAST comparison for sequencing results, and then analyzing and respectively deposited species according to comparison results. The foregoing corresponding lactobacilli are screened by screening low-pH growth tolerance test for the foregoing preserved 1,336 lactobacilli, 16S rRNA genotype screening, test for inhibition of *Gardnerella vaginalis*, lactic acid production test, hydrogen peroxide production test and test for adhesion on Hela cell test.

A method for screening the lactobacilli provided by the present disclosure includes the following steps:

1. Low-pH Growth Tolerance Test 1.1 Activation: activating the deposited lactobacilli in the MRS broth with a pH value of 6.5, and cultivating overnight at 37° C.;

1.2 Transferring: transferring an activated bacteria solution to the MRS broth with a pH value of 4-5, and measuring an $OD_{600}$ value once every 2-3 h;

1.3 Comparison of the $OD_{600}$ value: screening strains from different samples which can proliferate quickly or has the high $OD_{600}$ value.

2. 16S rRNA Genotype Screening

If the lactobacilli of the same species separated from the same sample have different 16S rRNA sequences, it is shown that their genotypes are different, and their physiological properties may be also different. Hence, the 16S rRNA genotype screening is carried out for the lactobacilli screened by the comparison of low-pH culture activities.

3. Test for Inhibition on *Gardnerella vaginalis*

After the lactobacilli are activated, taking 0.1 mL of bacteria solution to mix uniformly with the MRS solid medium, pouring into a 6 cm plate, cultivating for 48 h at 37° C. upon complete coagulation, taking out from the plate, and using a puncher with an inner diameter of 6 mm to punch an agar medium, so as to obtain bacteria cakes; and after the *Gardnerella vaginalis* is activated and transferred, diluting a *Gardnerella* solution to 100 times with the anaerobic sterile PBS buffer solution by ten consecutive gradients, respectively taking 0.5 mL of $10^{-1}$ and $10^{-2}$ diluents and 5.25 mL of BHI solid medium containing 5% horse serum for uniformly mixing, pouring into the 9 cm plate, slightly placing lactobacilli cakes on a BHI agar surface upon complete coagulation, symmetrically placing 4 cakes on every plate in the form of two in parallel, placing into an anaerobic seal pot, adding an anaeropack, forwardly placing the plate for 48 h-culture, and measuring a size of an inhibition zone with a vernier caliper.

4. Lactic Acid Production Test

After the lactobacilli are activated, transferring to the MRS broth medium in the form of two in parallel, cultivating for 48 h at 37° C., determining by a test paper with a pH value of 0.5-5.0, recording the pH value of the lactobacillus solution after the 48 h-culture, and selecting the strains for liquid chromatography by the following two conditions: Condition 1, the liquid chromatography is conducted for the strain with a pH value of 2.5; Condition 2, the strains with low pH values are selected from the same species of lactobacilli for liquid chromatography; after a liquid chromatography sample is determined, diluting a supernatant by 5 times, adding a concentrated sulfuric acid for pretreatment, and filtrating with a 0.22 μm needle filter before sampling. The related liquid chromatography parameters are as follows:

Model of instrument: Agilent, analytical liquid chromatograph 1200
Model of chromatographic column: Bio-Rad, Aminex™ HPX-87H.
Mobile phase: 0.005M $H_2SO_4$, at the speed of 0.6 mL/min
Detector and detection wave length: DAD, 207 nm; RID, differential refraction signal
Sample amount: 20 μL.

5. Hydrogen Peroxide Production Capacity

After the lactobacilli are activated, using a pipettor to suck 2 μL of bacteria solution to dibble into a MRS agar containing 0.25 mg/mL of 3,3',5,5'-tetramethyl benzidine solution and 0.01 mg/mL of horseradish peroxidase, providing two parallel plates at the observation time points of 24 h, 48 h and 72 h respectively, placing the plates at the same observation time point into the same anaerobic seal pot, putting into the anaeropack, cultivating at 37° C., taking out from the corresponding plates for exposure in the air upon the expiry of the corresponding culture time, observing a chromogenic reaction upon 30 min and photographing for recording; and taking *Lactobacillus delbrueckii* as a positive control, marking 4 points for those deeper than the blue produced by the *Lactobacillus delbrueckii*, 3 points for those equivalent to the blue produced by the *Lactobacillus delbrueckii*, 2 points for those shallower than the blue produced by the *Lactobacillus delbrueckii*, 1 point for those in very light blue (slight chromogenic reaction), and 0 points for non-discolouring.

6. Test for Adhesion on Hela Cells

After the lactobacilli are activated, centrifugally washing lactobacillus bodies twice, re-suspending with a PBS; sucking 100 μL of lactobacillus suspension into a 96-well cell culture plate containing the Hela cells; standing at 37° C. for 30-min incubation; washing twice with a sterile PBS to wash away non-adhesion lactobacilli; adding 25 μL of pancreatin solution into every well, and placing to a 37° C. incubator to digest cells; after the Hela cells are digested and turned into balls, adding 75 μL of complete medium into each well, repeatedly blowing and beating uniformly; sucking 20 μL of bacterial suspension after complete digesting, diluting with the sterile PBS by ten consecutive gradients, selecting the proper diluting gradient for a pouring-process counting experiment, and counting after cultivating at 37° C. for 48 h.

The ingredients and preparation methods of the above and following bacteria mediums are as follows: Preparation of a MRS broth: weighing 52.0 g of medium powder of a MRS finished product, and dissolving into 1 L of distilled water; heating and boiling, adding 0.55 g of cysteine hydrochloride after cooling to room temperature, and adjusting a pH value to 6.5 after stirring to dissolve; and installing a quantitative dispenser, feeding N2, heating until boiling, boiling for 20 min in a micro-boiling state, filling into 10 mL of anaerobic tubes after cooling, carrying out moist heat sterilization for 20 min at a high temperature of 118° C., and storing for further use in shade and away from light. Preparation of the MRS solid medium: weighing 52.0 g of medium powder of the MRS finished product and 15.0 g of agar powder, dissolving into 1 L of distilled water, heating until boiling, adding 0.55 g of cysteine hydrochloride to adjust the pH value to 6.5 after boiling, carrying out moist heat sterilization for 20 min at the high temperature of 118° C., and storing for further use in shade and away from light.

Preparation of a semi-quantitative hydrogen peroxide medium: weighing 52.0 g of medium powder of the MRS finished product and 15.0 g of agar powder, dissolving into 1 L of distilled water, adjusting the pH value to 6.5, carrying out moist heat sterilization for 20 min at the high temperature of 118° C., placing into a 50° C. water bath kettle to insulate for 30 min after sterilization, and adding TMB (a final concentration of the TMB is 0.25 mg/mL) and HRP (a final concentration of the HRP is 0.01 mg/mL) for uniformly mixing; and after cooling and coagulation, marking a culture name and a preparation date, and placing into a 4° C. refrigerator for further use.

Preparation of an anaerobic PBS: weighing 0.27 g of monopotassium phosphate, 1.42 g of disodium hydrogen phosphate, 8 g of sodium chloride and 0.2 g of potassium chloride, dissolving into 1 L of distilled water, heating until boiling, adding 0.55 g of cysteine hydrochloride after cooling to room temperature, adjusting the pH value to 6.5 after stirring and dissolving, installing the quantitative dispenser and feeding N2, heating until boiling, boiling for 30 min in a micro-boiling state, filling to 10 mL anaerobic tubes after cooling, carrying out moist heat sterilization for 30 min at a high temperature of 121° C., and storing for further use in shade and away from light.

Preparation of an anaerobic BHI liquid medium: weighing 37.0 g of medium powder of a BHI finished product, dissolving into 1 L of distilled water, heating until boiling, adding 0.55 g of cysteine hydrochloride after cooling to room temperature, adjusting the pH value to 6.5 after stirring and dissolving, installing the quantitative dispenser and feeding N2, heating until boiling, boiling for 20 min in a micro-boiling state, feeding N2 and CO2 (a ratio of 1:1) in the course of cooling and filling, filling to 10 mL anaerobic tubes after cooling, carrying out moist heat sterilization for 20 min at a high temperature of 118° C., and storing for further use in shade and away from light.

Preparation of an anaerobic BHI semi-solid medium: weighing 37.0 g of medium powder of the BHI finished product, and dissolving into 1 L of distilled water; heating until boiling, adding 6 g of agar powder and 0.55 g of cysteine hydrochloride after cooling to room temperature, adjusting the pH value to 6.5 after stirring and dissolving, installing the quantitative dispenser and feeding N2, heating until boiling, boiling for 20 min in the micro-boiling state, feeding N2 and CO2 (a ratio of 1:1) in the course of cooling and filling, filling to 10 mL anaerobic tubes in time, carrying out moist heat sterilization for 20 min at a high temperature of 118° C., and storing in shade and away from light.

Preparation of a nutrient broth liquid medium: weighing 10 g of peptone, 3 g of beef powder, 5 g of sodium chloride, dissolving into 1 L of distilled water, adjusting a pH value to 7.2, heating until boiling, and dispensing after cooling to room temperature, 10 mL for each one; and carrying out moist heat sterilization for 15 min at a high temperature of 121° C., and storing in shade and away from light. Preparation of a nutrient broth solid medium: weighing 10 g of peptone, 3 g of beef powder, 5 g of sodium chloride and 6 g of agar powder, dissolving into 1 L of distilled water, adjusting the pH to 7.2, slightly cooling, and filling into the 10 mL anaerobic tubes in time; and carrying out moist heat sterilization for 15 min at a high temperature of 121° C., and storing in shade and away from light. For convenient description, the following *Lactobacillus johnsonii* Ljohn-1 (Deposition No.: CCTCC No. 2019426) is hereinafter referred to as "A"; the *Lactobacillus crispatus* Lcris-2 (Deposition No.: CCTCC No. 2019427) is hereinafter referred to as "B"; the *Lactobacillus rhamnosus* Lrham-6 (Deposition No.: CCTCC No. 2019428) is hereinafter referred to as "C"; the *Lactobacillus jensenii* Ljen-10 (Deposition No.: CCTCC No. 2019429) is hereinafter referred to as "D"; and the *Lactobacillus gasseri* Lgass-17 (Deposition No.: CCTCC No. 2019430) is hereinafter referred to as "E".

Embodiment 1: Comparison of Lactic Acid Production Capacities of Single and Combined Lactobacilli Single lactobacilli: After the lactobacilli are activated, transfer to a MRS broth medium in the form of two in parallel, cultivate for 48 h at 37° C., determine by a test paper with a pH value of 0.5-5.0, record a pH value of a lactobacillus solution after the 48 h culture, carry out liquid chromatography for strains, dilute a supernatant by 5 times, add a concentrated sulfuric acid for pretreatment, and filtrate with a 0.22 μm syringe-driven filter before sampling.

Combined lactobacilli: After the lactobacilli are activated and transferred, select three or more of strains for mixed culture in the form of three in parallel, cultivate for 48 h at 37° C., centrifuge, dilute the supernatant by 5 times, add the concentrated sulfuric acid for pretreatment, and filtrate with the 0.22 μm syringe-driven filter before sampling. The related liquid chromatography parameters are as follows:

Model of instrument: Agilent, analytical liquid chromatograph 1200
Model of chromatographic column: Bio-Rad, Aminex™-HPX-87H
Mobile phase: 0.005M $H_2SO_4$, at the speed of 0.6 mL/min
Detector and detection wave length: DAD, 207 nm; RID, differential refraction signal
Sample amount: 20 μL.

Embodiment 2: Comparison of Hydrogen Peroxide Production Capacities of Single and Combined Lactobacilli Single lactobacilli: After the lactobacilli are activated, use a pipettor to suck 2 μL of bacteria solution to dibble into a MRS agar containing 0.25 mg/mL of 3,3',5,5'-tetramethyl benzidine solution and 0.01 mg/mL of horseradish peroxidase, provide two parallel plates at the observation time points of 24 h, 48 h and 72 h respectively, place the plates at the same observation time point into the same anaerobic seal pot, cultivate at 37° C., take out from the corresponding plates for exposure in the air upon the expiry of the corresponding culture time, observe a chromogenic reaction upon 30 min and photographing for recording: taking *Lactobacillus delbrueckii* as a positive control, marking 4 points for those deeper than the blue produced by the *Lactobacillus delbrueckii*, 3 points for those equivalent to the blue produced by the *Lactobacillus delbrueckii*, 2 points for those shallower than the blue produced by the *Lactobacillus delbrueckii*, 1 point for those in very light blue (slight chromogenic reaction), and 0 points for non-discolouring.

Combined lactobacilli: After the lactobacilli are activated and transferred, select three or more strains for mixing, use the pipettor to suck 2 μL of bacteria solution to dibble into the MRS agar containing TMB and HRP, cultivate at 37° C., take out from the corresponding plates for exposure in the air upon the expiry of the corresponding culture time, observe a chromogenic reaction upon 30 min and photograph for recording: taking *Lactobacillus delbrueckii* as the positive control, marking 4 points for those deeper than the blue produced by the *Lactobacillus delbrueckii*, 3 points for those equivalent to the blue produced by the *Lactobacillus delbrueckii*, 2 points for those shallower than the blue produced by the *Lactobacillus delbrueckii*, 1 point for those in very light blue (slight chromogenic reaction), and 0 points for non-discolouring.

Embodiment 3: Comparison of *Gardnerella vaginalis* Inhibitions of Single and Combined Lactobacilli Single lactobacilli: After the lactobacilli are activated, take 0.1 mL of bacteria solution to mix uniformly with the MRS solid medium, pour into a 6 cm plate, cultivate for 48 h at 37° C. upon complete coagulation, take out from the plate, and use a puncher with an inner diameter of 6 mm to punch an agar medium, so as to obtain bacteria cakes; and after the *Gardnerella vaginalis* is activated and transferred, dilute a *gardnerella* solution to 100 times with the anaerobic sterile PBS buffer solution by ten consecutive gradients, respectively take 0.5 mL of $10^{-1}$ and $10^{-2}$ diluents and 5.25 mL of BHI solid medium containing 5% horse serum for uniformly mixing, pour into the 9 cm plate, slightly place lactobacillus cakes on a BHI agar surface upon complete coagulation, symmetrically place 4 bacteria cakes on every plate in the form of two in parallel, place into an anaerobic seal pot, add an anaeropack, forwardly place the plate to cultivate for 48 h, and measure a size of an inhibition zone with a vernier caliper.

Combined lactobacilli: After the lactobacilli are activated and transferred, select three or more strains for mixing, take 0.1 mL of bacteria solution to mix uniformly with the MRS solid medium, pour into a 6 cm plate, cultivate for 48 h at 37° C. upon complete coagulation, take out from the plate, and use a puncher with the inner diameter of 6 mm to punch the agar medium, so as to obtain the bacteria cake; and after the *Gardnerella vaginalis* is activated and transferred, dilute a *gardnerella* solution to 100 times with the anaerobic sterile PBS buffer solution by ten consecutive gradients, respectively take 0.5 mL of 10-1 and 10-2 diluents and 5.25 mL of BHI solid medium containing 5% horse serum for uniformly mixing, pour into the 9 cm plate, slightly place lactobacillus cakes on a BHI agar surface upon complete coagulation, symmetrically place 4 bacteria cakes on every plate in the form of two in parallel, place into an anaerobic seal pot, add an anaeropack, forwardly place the plate to cultivate for 48 h, and measure a size of an inhibition zone with a vernier caliper.

Embodiment 4: Comparison of Adhesion on Hela Cells by Single Bacteria and Combined Bacteria Single bacteria: After the lactobacilli are activated, centrifugally wash lactobacillus bodies twice, and re-suspend with a PBS; suck 100 μL of lactobacillus suspension into a 96-well cell culture plate containing Hela cells, stand at 37° C. for incubation for 30 min, and wash twice with the sterile PBS after 30 min to wash away non-adhesion lactobacilli; add 25 μL of pancreatin solution into every well of the 96-well cell culture plate containing the Hela cells, and place to a 37° C. incubator to digest cells; after the Hela cells are digested and turned into balls, add 75 μL of complete medium into each well, and repeatedly blow and beat uniformly; suck 20 μL of bacterial suspension after complete digesting, dilute with the sterile PBS by ten consecutive gradients, select the proper diluting gradient for a pouring-process counting experiment, and count after cultivating at 37° C. for 48 h.

Combined bacteria: After the lactobacilli are activated and transferred, centrifugally wash bacteria bodies twice, re-suspend with a PBS, select bacteria solution of three or more strains for mixing uniformly, suck 100 μL of lactobacillus suspension into the 96-well cell culture plate containing the Hela cells, stand at 37° C. for incubation for 30 min and 4 h, and wash with the sterile PBS twice upon 30 min and 4 h to wash away non-adhered lactobacilli; upon expiry of the corresponding incubation time, add 25 μL of pancreatin solution into each well of the 96-well cell culture plate containing the Hela cells, and place into the 37° C. incubator to digest cells; after the Hela cells are digested and turned into balls, add 75 μL of complete medium into each well, and repeatedly blow and beat uniformly; suck 20 μL of bacterial suspension after complete digesting, dilute with the sterile PBS by ten consecutive gradients, select the $10^{-4}$ diluting gradient for a pouring-process counting experiment, and count after cultivating at 37° C. for 48 h.

Embodiment 5: Comparison of Inhibitions on *Staphylococcus aureus, Pseudomonas aeruginosa, Escherichia coli, Salmonella paratyphi* B and *Shigella dysenteriae* by Single Bacteria and Combined Bacteria Single lactobacilli: After the lactobacilli are activated, take 0.1 mL of bacteria solution to mix uniformly with the MRS solid medium, pour into a 6 cm plate, cultivate for 48 h at 37° C. upon complete coagulation, take out from the plate, and use a puncher with an inner diameter of 6 mm to punch an agar medium, so as to obtain bacteria cakes; and After the *Staphylococcus aureus*, the *Pseudomonas aeruginosa*, the *Escherichia coli*, the *Salmonella* paratyphi B and the *Shigella dysenteriae* are activated and transferred, dilute a pathogenic bacteria solution to 100 times with 0.9% normal saline (NS) by ten consecutive gradients, respectively take 0.5 mL of $10^{-1}$ and $10^{-2}$ diluents and 5 mL of nutrient agar solid medium for uniformly mixing, pour into a 9 cm plate, slightly place lactobacilli cakes on a nutrient agar surface upon complete coagulation, symmetrically place 4 cakes on every plate in the form of two in parallel, place into a seal pot, forwardly place the plate to cultivate for 24 h, and measure a size of an inhibition zone with a vernier caliper.

Combined Bacteria: Inhibition on *Salmonella paratyphi* B and *Shigella dysenteriae*

After the lactobacilli are activated and transferred, select three or more strains for mixing, take 0.1 mL of bacteria solution to mix uniformly with a MRS solid medium, pour into a 6 cm plate, cultivate for 48 h at 37° C. upon complete coagulation, take out from the plate, and use a puncher with an inner diameter of 6 mm to punch an agar medium, so as to obtain bacteria cakes; and after the *Staphylococcus aureus*, the *Staphylococcus aureus*, the *Pseudomonas aeruginosa*, the *Escherichia coli*, the *Salmonella* paratyphi B and the *Shigella dysenteriae* are activated and transferred, dilute the pathogenic bacteria solution to 100 times with 0.9% normal saline (NS) by ten consecutive gradients, respectively take 0.5 mL of $10^{-1}$ and $10^{-2}$ diluents and 5 mL of nutrient agar solid medium for uniformly mixing, pour into a 9 cm plate, slightly place lactobacilli cakes on a nutrient agar surface upon complete coagulation, symmetrically place 4 cakes on every plate in the form of two in parallel, place into a seal pot, forwardly place the plate to cultivate for 24 h, and measure a size of an inhibition zone with a vernier caliper.

According to comparison experiments in the foregoing Embodiments 1-5, the comparison results are shown in Table 6 below:

TABLE 6

Comparison of probiotic abilities of single bacteria and combined bacteria

| Microorganism description | Microbiological composition (number before the letter expresses content ratio of single strain corresponding to the letter) | Diameteter of inhibition zone of *Gardnerella* (mm) | Rating of hydrogen peroxide capacity | Content of lactic acid (mg/L) | Adhesion number of single cells |
|---|---|---|---|---|---|
| DS | *Lactobacillus delbrueckii* | 14.29 | 3 | 12964.12 | 7.7 |
| A | A | 17.77 | 1 | 16064.53 | 5.95 |
| B | B | 10.19 | 1 | 16098.44 | 13.2 |
| C | C | 14.71 | 0 | 18001.19 | 8.3 |
| D | D | 15.06 | 4 | 14258.47 | 27.15 |
| E | E | 16.63 | 1 | 14219.11 | 17.8 |
| 1 | 1A + 1B + 1D | 19.87 | 4 | 15117.36 | 8.91 |
| 2 | 1A + 1B + 1C | 19.50 | 0 | 17555.32 | 7.5 |
| 3 | 1A + 1B + 1E | 19.65 | 0 | 13703.73 | 1.64 |
| 4 | 1B + 1C + 1D | 19.65 | 4 | 17224.19 | 18.83 |
| 5 | 1B + 1D + 1E | 19.81 | 4 | 15562.84 | 7.5 |
| 6 | 1B + 1C + 1E | 19.34 | 0 | 17479.38 | 34.67 |
| 7 | 1A + 1C + 1D | 19.16 | 4 | 16974.68 | 49.68 |
| 8 | 1A + 1C + 1E | 19.31 | 0 | 17012.27 | 8.75 |
| 9 | 1A + 1D + 1E | 19.42 | 4 | 16769.17 | 19.14 |
| 10 | 1C + 1D + 1E | 19.58 | 4 | 16794.06 | 43.5 |
| 11 | 1A + 1B + 1C + 1D | 19.50 | 4 | 17203.57 | 12.67 |
| 12 | 1A + 1B + 1C + 1E | 19.35 | 0 | 17023.87 | 13.58 |
| 13 | 1A + 1B + 1D + 1E | 19.50 | 4 | 13091.07 | 20.08 |
| 14 | 1B + 1C + 1D + 1E | 19.46 | 4 | 16653.29 | 14.42 |
| 15 | 1A + 1C + 1D + 1E | 19.13 | 4 | 13642.85 | 36.42 |
| 16 | 1A + 1B + 1C + 1D + 1E | 19.11 | 4 | 16618.79 | 12.17 |

| Microorganism description | Diameter of inhibition zone of *Staphylococcus aureus* (mm) | Diameter of inhibition zone of *Escherichia coli* (mm) | Diameter of inhibition zone of *Shigella dysenteriae* (mm) | Diameter of inhibition zone of *Psuedomonas aeruginosa* (mm) | Diameter of inhibition zone of *Salmonella paratyphi B* (mm) |
|---|---|---|---|---|---|
| DS | 11.28 | 9.32 | 11.93 | 13.09 | 12.00 |
| A | 12.39 | 9.65 | 12.41 | 13.28 | 12.45 |
| B | 12.61 | 10.51 | 12.41 | 13.74 | 12.01 |
| C | 13.09 | 11.26 | 12.85 | 14.46 | 11.01 |
| D | 9.61 | 7.30 | 12.26 | 12.92 | 11.78 |
| E | 12.61 | 9.29 | 10.98 | 12.00 | 11.52 |
| 1 | 12.99 | 10.83 | 13.29 | 14.76 | 13.65 |
| 2 | 13.47 | 12.26 | 13.58 | 15.84 | 14.52 |
| 3 | 12.68 | 11.94 | 15.83 | 15.76 | 13.75 |
| 4 | 14.16 | 12.40 | 13.55 | 14.34 | 14.47 |
| 5 | 13.05 | 9.55 | 12.24 | 14.49 | 13.40 |
| 6 | 13.35 | 10.17 | 13.85 | 15.30 | 12.58 |
| 7 | 13.03 | 9.33 | 16.37 | 15.28 | 13.66 |
| 8 | 13.53 | 10.52 | 15.72 | 15.59 | 12.54 |
| 9 | 13.03 | 10.85 | 14.75 | 15.48 | 13.64 |
| 10 | 12.78 | 11.20 | 13.67 | 15.28 | 12.74 |
| 11 | 12.59 | 10.61 | 13.49 | 14.75 | 12.55 |
| 12 | 13.62 | 11.50 | 15.58 | 15.59 | 13.40 |
| 13 | 14.18 | 11.68 | 15.23 | 15.62 | 14.25 |
| 14 | 12.06 | 10.81 | 13.59 | 14.63 | 12.36 |
| 15 | 12.17 | 10.61 | 13.73 | 15.01 | 12.59 |
| 16 | 12.84 | 11.13 | 13.94 | 14.82 | 12.96 |

Embodiment 6: Test for Antagonistic and Symbiotic Effects Among all Strains in the Multi-Lactobacillus Use one of strains to be determined to draw a straight line on a medium plate, transversely inoculate two of strains to be determined at both sides of the one of strains to be determined, cultivate for 18-24 h in a cross manner, and determine a bacteriostatic width of a cross point.

Though the tests, the results of antagonistic and symbiotic effects among all strains (bacteriostatic semi-diameter: mm) are shown in Table 7:

TABLE 7

Diameters (mm) of Symbiotic Inhibition Zones of All Single Bacteria on Solid Plate

|   | A | B | C | D | E |
|---|---|---|---|---|---|
| A | 0.00 | 0.00 | 0.00 | 0.00 | 0.00 |
| B | 0.00 | 0.00 | 0.00 | 0.00 | 0.00 |
| C | 0.00 | 0.00 | 0.00 | 0.00 | 0.00 |
| D | 0.00 | 0.00 | 0.00 | 0.00 | 0.00 |
| E | 0.00 | 0.00 | 0.00 | 0.00 | 0.00 |

Inoculate the single strain to be determined to a MRS broth, cultivate at 37° C. for 8 h, dilute the single strain to a proper gradient by ten consecutive gradients before inoculation, count a concentration of the bacteria solution before inoculation in such a manner of three in parallel at every gradient, place the plate into an anaerobic seal pot, put an anaeropack, and cultivate at 37° C. for 48 h; inoculate the strains to be determined to the MRS broth after mixing, wherein an inoculation concentration of each bacterium in the mixed bacteria is the same as an inoculation concentration of the single strain, and cultivate at 37° C. for 8 h; dilute the single and mixed bacteria MRS broths, after being cultivated for about 8 h, to the proper gradient by ten consecutive gradients, coat and count in such a manner of three parallel at every gradient, place the plate into the anaerobic seal pot, put an anaeropack, and cultivate at 37° C. for 48 h; after the plate is cultivated for 48 h anaerobically, calculate bacterial colonies before and after inoculation for the single bacteria plate, and analyze amplification multiples of the single bacteria; and meanwhile, carry out mass spectrum identification for the flora on the mixed bacteria plate, determine species through a mass spectrum to analyze the amplification multiple of the single bacteria in the mixed bacteria, and prove no inhibition among the strains but they may grow together through the tests, see Table 8 for broth co-culture amplification data.

TABLE 8

Amplification Multiples of Symbiotic Single Bacteria on MRS Broth

| Strain No. | Amplification multiples calculated by mixed culture mass spectrum-parallel 1 | Amplification multiples calculated by mixed culture mass spectrum-parallel 2 | Amplification multiples calculated by single bacteria culture |
|---|---|---|---|
| A | 14.73 | 10.85 | 17.17 |
| B | 9.74 | 12.82 | 17.57 |
| C | 85.08 | 81.73 | 92.15 |
| D | 38.22 | 51.4 | 29.06 |
| E | 75.19 | 71.3 | 103.69 |

The present disclosure may be implemented well according to the foregoing embodiments. It should be noted that, to solve the same technical problem, the applied technical solution is essentially the same as the present disclosure under the premise of the aforesaid structure design even if some insubstantial modifications or improvements are made for the present disclosure, so that the technical solution should fall within the protection scope of the present disclosure.

The invention claimed is:

1. A multi-*lactobacillus* composition comprising at least three of the following *lactobacillus* strains: *Lactobacillus johnsonii*, *Lactobacillus gasseri*, *Lactobacillus rhamnosus*, *Lactobacillus crispatus* and *Lactobacillus jensenii*;
wherein the multi-*lactobacillus* composition is lyophilized;
wherein the *Lactobacillus johnsonii* is *Lactobacillus johnsonii* CCTCC No. 2019426; the *Lactobacillus gasseri* is *Lactobacillus gasseri* CCTCC No. 2019430; the *Lactobacillus rhamnosus* is *Lactobacillus rhamnosus* CCTCC No. 2019428; the *Lactobacillus crispatus* is *Lactobacillus crispatus* CCTCC No. 2019427; and the *Lactobacillus jensenii* is *Lactobacillus jensenii* CCTCC No. 2019429, and
the multi-*lactobacillus* composition possesses a higher inhibitory activity against *Gardnerella vaginalis* than any one of the single *lactobacillus* strains.

2. The multi-*lactobacillus* composition according to claim 1, wherein a viable count of the composition is $10^5$-$10^{11}$ CFU/g, and a content of each lactobacillus strain is not lower than $10^5$ CFU/g.

3. A fermentation broth comprising the multi-*lactobacillus* composition according to claim 2.

4. A method for preventing or treating pathogenic bacteria of bacterial vaginosis (BV), comprising administering an effective amount of the composition according to claim 1 to a subject in need thereof.

5. A method of preparation of sanitary articles for pudendum, comprising providing and preparing the composition according to claim 1 and applying the composition according to claim 1 to sanitary articles.

6. A method for adjusting the balance of vaginal flora, comprising administering an effective amount of the composition according to claim 1 to a subject in need thereof.

7. A method for preventing or treating pathogenic bacteria, comprising administering an effective amount of the composition according to claim 1 to a subject in need thereof, wherein the pathogenic bacteria include at least one selected from the group consisting of: *Gardnerella vaginalis, Staphylococcus aureus, Pseudomonas aeruginosa, Escherichia coli, Salmonella* paratyphi B and *Shigella dysenteriae*.

8. A method for preparation of external care products for infants delivered by caesarean section, comprising providing and preparing the composition according to claim 1 and applying said composition to external care products for infants delivered by caesarean section.

9. A method for preventing or treating pathogenic bacteria of bacterial vaginosis (BV), comprising administering an effective amount of the fermentation broth according to claim 3 to a subject in need thereof.

10. A method for preparation of sanitary articles for pudendum, comprising providing and preparing the fermentation broth according to claim 3 and applying said fermentation broth to sanitary articles.

11. A method for adjusting the balance of vaginal flora, comprising administering an effective amount of the fermentation broth according to claim 3 to a subject in need thereof.

12. A method for preventing or treating pathogenic bacteria, comprising administering an effective amount of the fermentation broth according to claim 3 to a subject in need thereof, wherein the pathogenic bacteria include at least one selected from the group consisting of: *Gardnerella vaginalis, Staphylococcus aureus, Pseudomonas aeruginosa, Escherichia coli, Salmonella* paratyphi B and *Shigella dysenteriae*.

13. A method for preparation of external care products for infants delivered by caesarean section, comprising providing and preparing the fermentation broth according to claim 3 and applying said composition to external care products for infants delivered by caesarean section.

14. The multi-*lactobacillus* composition according to claim 1, wherein the composition comprises *lactobacillus* strains selected from the group consisting of:
*Lactobacillus* crispatus CCTCC No. 2019427, *Lactobacillus rhamnosus* CCTCC No. 2019428 and *Lactobacillus jensenii* CCTCC No. 2019429;
*Lactobacillus johnsonii* CCTCC No. 2019426, *Lactobacillus rhamnosus* CCTCC No. 2019428 and *Lactobacillus jensenii* CCTCC No. 2019429;
*Lactobacillus johnsonii* CCTCC No. 2019426, *Lactobacillus jensenii* CCTCC No. 2019429 and *Lactobacillus* gasseri CCTCC No. 2019430;
*Lactobacillus rhamnosus* CCTCC No. 2019428, *Lactobacillus jensenii* CCTCC No. 2019429 and *Lactobacillus* gasseri CCTCC No. 2019430;
*Lactobacillus johnsonii* CCTCC No. 2019426, *Lactobacillus* crispatus CCTCC No. 2019427, *Lactobacillus rhamnosus* CCTCC No. 2019428 and *Lactobacillus jensenii* CCTCC No. 2019429;
*Lactobacillus johnsonii* CCTCC No. 2019426, *Lactobacillus* crispatus CCTCC No. 2019427, *Lactobacillus jensenii* CCTCC No. 2019429 and *Lactobacillus* gasseri CCTCC No. 2019430;
*Lactobacillus* crispatus CCTCC No. 2019427, *Lactobacillus rhamnosus* CCTCC No. 2019428, *Lactobacillus jensenii* CCTCC No. 2019429 and *Lactobacillus* gasseri CCTCC No. 2019430; *Lactobacillus johnsonii* CCTCC No. 2019426, *Lactobacillus rhamnosus* CCTCC No. 2019428, *Lactobacillus jensenii* CCTCC No. 2019429 and *Lactobacillus* gasseri CCTCC No. 2019430; and
*Lactobacillus johnsonii* CCTCC No. 2019426, *Lactobacillus* gasseri CCTCC No. 2019430, *Lactobacillus rhamnosus* CCTCC No. 2019428, *Lactobacillus* crispatus CCTCC No. 2019427, and *Lactobacillus jensenii* CCTCC No. 2019429.

15. The multi-*lactobacillus* composition according to claim 1, wherein the composition comprises *lactobacillus* strains selected from the group consisting of:
*Lactobacillus johnsonii* CCTCC No. 2019426, *Lactobacillus* crispatus CCTCC No. 2019427, *Lactobacillus rhamnosus* CCTCC No. 2019428 and *Lactobacillus jensenii* CCTCC No. 2019429;
*Lactobacillus johnsonii* CCTCC No. 2019426, *Lactobacillus* crispatus CCTCC No. 2019427, *Lactobacillus jensenii* CCTCC No. 2019429 and *Lactobacillus* gasseri CCTCC No. 2019430;
*Lactobacillus* crispatus CCTCC No. 2019427, *Lactobacillus rhamnosus* CCTCC No. 2019428, *Lactobacillus jensenii* CCTCC No. 2019429 and *Lactobacillus* gasseri CCTCC No. 2019430;
*Lactobacillus johnsonii* CCTCC No. 2019426, *Lactobacillus rhamnosus* CCTCC No. 2019428, *Lactobacillus jensenii* CCTCC No. 2019429 and *Lactobacillus* gasseri CCTCC No. 2019430; and
*Lactobacillus johnsonii* CCTCC No. 2019426, *Lactobacillus* gasseri CCTCC No. 2019430, *Lactobacillus rhamnosus* CCTCC No. 2019428, *Lactobacillus* crispatus CCTCC No. 2019427 and *Lactobacillus jensenii* CCTCC No. 2019429.

16. The multi-*lactobacillus* composition according to claim 1, wherein the composition comprises the *lactobacillus* strains
*Lactobacillus johnsonii* CCTCC No. 2019426, *Lactobacillus* crispatus CCTCC No. 2019427, *Lactobacillus jensenii* CCTCC No. 2019429 and *Lactobacillus* gasseri CCTCC No. 2019430.

17. The multi-*lactobacillus* composition according to claim 1, wherein the composition comprises the *lactobacillus* strains
*Lactobacillus johnsonii* CCTCC No. 2019426 *Lactobacillus* gasseri CCTCC No. 2019430, *Lactobacillus rhamnosus* CCTCC No. 2019428, *Lactobacillus* crispatus CCTCC No. 2019427 and *Lactobacillus jensenii* CCTCC No. 2019429.

* * * * *